United States Patent
Szlavik et al.

(10) Patent No.: US 10,227,358 B2
(45) Date of Patent: Mar. 12, 2019

(54) HYDROXYESTER DERIVATIVES, A PROCESS FOR THEIR PREPARATION AND PHARMACEUTICAL COMPOSITIONS CONTAINING THEM

(71) Applicants: LES LABORATOIRES SERVIER, Suresnes (FR); VERNALIS (R&D) LTD, Winnersh (GB)

(72) Inventors: Zoltan Szlavik, Budapest (HU); András Kotschy, Törökbálint (HU); Maïa Chanrion, Issy les Moulineaux (FR); Didier Demarles, Chécu (FR); Olivier Geneste, Rueil-Malmaison (FR); James Edward Paul Davidson, Great Shelford (GB); James Brooke Murray, Linton (GB); Szabolcs Sipos, Budapest (HU); Attila Paczal, Budapest (HU); Balazs Balint, Fot (HU)

(73) Assignees: LES LABORATOIRES SERVIER, Suresnes (FR); VERNALIS &R&D) LTD., Winnersh, Berkshire (GB)

( * ) Notice: Subject to any disclaimer, the term of this patent is extended or adjusted under 35 U.S.C. 154(b) by 0 days.

(21) Appl. No.: 15/737,479

(22) PCT Filed: Jun. 22, 2016

(86) PCT No.: PCT/EP2016/064433
§ 371 (c)(1),
(2) Date: Dec. 18, 2017

(87) PCT Pub. No.: WO2016/207225
PCT Pub. Date: Dec. 29, 2016

(65) Prior Publication Data
US 2018/0170947 A1     Jun. 21, 2018

(30) Foreign Application Priority Data

Jun. 23, 2015 (FR) ...................... 15 55752

(51) Int. Cl.
| | |
|---|---|
| *C07D 495/04* | (2006.01) |
| *A61P 35/00* | (2006.01) |
| *A61K 31/519* | (2006.01) |
| *A61K 45/06* | (2006.01) |

(52) U.S. Cl.
CPC .......... *C07D 495/04* (2013.01); *A61K 31/519* (2013.01); *A61K 45/06* (2013.01); *A61P 35/00* (2018.01)

(58) Field of Classification Search
CPC .................................................. C07D 495/04
See application file for complete search history.

(56) References Cited

U.S. PATENT DOCUMENTS 9,670,227 B2 *  6/2017  Kotschy ............... C07D 495/04

FOREIGN PATENT DOCUMENTS

| CN | 102464667 | 5/2012 |
|---|---|---|
| EP | 2886545 | 6/2015 |
| WO | WO2013072694 | 5/2013 |

OTHER PUBLICATIONS

International Search Report from PCT/EP2016/064433 dated Aug. 24, 2016.
Kemnitzer, William, et al., "Discovery of 4-anilino-N-methylthieno[3,2-d]pyrimidines and 4-anilino-N-methylthieno[2,3-d]pyrimidines as potent apoptosis inducers", Bioorganic & Medicinal Chemistry Letters, 19 (2009), pp. 3536-3540.

\* cited by examiner

*Primary Examiner* — Bruck Kifle
(74) *Attorney, Agent, or Firm* — Hueschen and Sage

(57) ABSTRACT

Compounds of formula (I):

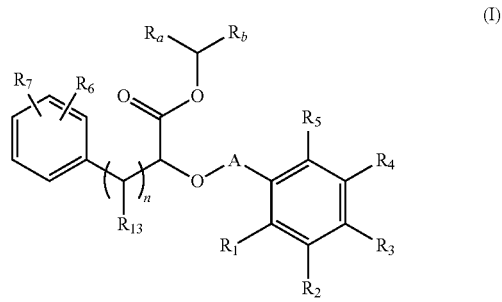

wherein $R_1$, $R_2$, $R_3$, $R_4$, $R_5$, $R_6$, $R_7$, $R_{13}$, $R_a$, $R_b$, A and n are as defined in the description.
Medicinal products containing the same which are useful in treating conditions requiring a pro-apoptotic agent.

44 Claims, No Drawings

HYDROXYESTER DERIVATIVES, A PROCESS FOR THEIR PREPARATION AND PHARMACEUTICAL COMPOSITIONS CONTAINING THEM

The present invention relates to new hydroxyester derivatives, to a process for their preparation and to pharmaceutical compositions containing them.

The compounds of the present invention are new and have very valuable pharmacological characteristics in the field of apoptosis and cancerology.

Apoptosis, or programmed cell death, is a physiological process that is crucial for embryonic development and maintenance of tissue homeostasis.

Apoptotic-type cell death involves morphological changes such as condensation of the nucleus, DNA fragmentation and also biochemical phenomena such as the activation of caspases which cause damage to key structural components of the cell, so inducing its disassembly and death. Regulation of the process of apoptosis is complex and involves the activation or repression of several intracellular signalling pathways (Cory S. et al., Nature Review Cancer 2002, 2, 647-656).

Deregulation of apoptosis is involved in certain pathologies. Increased apoptosis is associated with neurodegenerative diseases such as Parkinson's disease, Alzheimer's disease and ischaemia. Conversely, deficits in the implementation of apoptosis play a significant role in the development of cancers and their chemoresistance, in auto-immune diseases, inflammatory diseases and viral infections. Accordingly, absence of apoptosis is one of the phenotypic signatures of cancer (Hanahan D. et al., Cell 2000, 100, 57-70).

The anti-apoptotic proteins of the Bcl-2 family are associated with numerous pathologies. The involvement of proteins of the Bcl-2 family is described in numerous types of cancer, such as colon cancer, breast cancer, small-cell lung cancer, non-small-cell lung cancer, bladder cancer, ovarian cancer, prostate cancer, chronic lymphoid leukaemia, lymphoma, myeloma, acute myeloid leukemia, pancreatic cancer, etc. Overexpression of the anti-apoptotic proteins of the Bcl-2 family is involved in tumorigenesis, in resistance to chemotherapy and in the clinical prognosis of patients affected by cancer. Notably, Mcl-1, an anti-apoptotic Bcl-2 family member, is overexpressed in various types of cancer (Beroukhim R. et. al., Nature 2010, 899-905). There is, therefore, a therapeutic need for compounds that inhibit the anti-apoptotic activity of the proteins of the Bcl-2 family.

In addition to being new, the compounds of the present invention have pro-apoptotic properties making it possible to use them in pathologies involving a defect in apoptosis, such as, for example, in the treatment of cancer and of immune and auto-immune diseases.

The present invention relates more especially to compounds of formula (I):

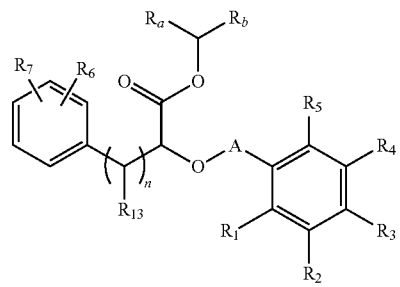

wherein:
A represents the group

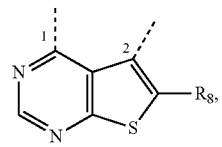

in which 1 is linked to the oxygen atom and 2 is linked to the phenyl ring, $R_1$ represents a linear or branched ($C_1$-$C_6$)alkyl group, a linear or branched ($C_2$-$C_6$)alkenyl group, a linear or branched ($C_2$-$C_6$)alkynyl group, a linear or branched ($C_1$-$C_6$)alkoxy group, a —S—($C_1$-$C_6$)alkyl group, a linear or branched ($C_1$-$C_6$)polyhaloalkyl, a hydroxy group, a hydroxy($C_1$-$C_6$)alkyl group, a cyano group, —$NR_{11}R_{11}$', —$Cy_6$, or a halogen atom, $R_2$, $R_3$, $R_4$ and $R_5$ independently of one another represent a hydrogen atom, a halogen atom, a linear or branched ($C_1$-$C_6$)alkyl group, a linear or branched ($C_2$-$C_6$)alkenyl group, a linear or branched ($C_2$-$C_6$)alkynyl group, a linear or branched ($C_1$-$C_6$)polyhaloalkyl, a hydroxy group, a hydroxy($C_1$-$C_6$)alkyl group, a linear or branched ($C_1$-$C_6$)alkoxy group, a —S—($C_1$-$C_6$)alkyl group, a cyano group, a nitro group, -alkyl($C_0$-$C_6$)—$NR_9R_9$', —O-alkyl($C_1$-$C_6$)—$NR_9R_9$', —O-alkyl($C_1$-$C_6$)—$R_{10}$, —C(O)—$OR_9$, —O—C(O)—$R_9$, —C(O)—$NR_9R_9$', —$NR_9$—C(O)—$R_9$', —$NR_9$—C(O)—$OR_9$', -alkyl($C_1$-$C_6$)—$NR_9$—C(O)—$R_9$', —$SO_2$—$NR_9R_9$', —$SO_2$-alkyl($C_1$-$C_6$), or the substituents of one of the pairs ($R_2$, $R_3$), ($R_3$, $R_4$), ($R_4$, $R_5$), when grafted onto two adjacent carbon atoms, form together with the carbon atoms carrying them an aromatic or non-aromatic ring composed of from 5 to 7 ring members, which may contain from 1 to 3 heteroatoms selected from oxygen, sulphur and nitrogen, it being understood that resulting ring may be substituted by a group selected from a linear or branched ($C_1$-$C_6$)alkyl group, —$NR_{11}R_{11}$', -alkyl($C_0$-$C_6$)—$Cy_1$, or an oxo, $R_6$ and $R_7$ independently of one another represent a hydrogen atom, a halogen atom, a linear or branched ($C_1$-$C_6$)alkyl group, a linear or branched ($C_2$-$C_6$)alkenyl group, a linear or branched ($C_2$-$C_6$)alkynyl group, a linear or branched ($C_1$-$C_6$)polyhaloalkyl, a hydroxy group, a linear or branched ($C_1$-$C_6$)alkoxy group, a —S—($C_1$-$C_6$)alkyl group, a cyano group, a nitro group, -alkyl($C_0$-$C_6$)—$NR_9R_9$', —O-alkyl($C_1$-$C_6$)—$NR_9R_9$', —O—$Cy_1$, -alkyl($C_0$-$C_6$)—$Cy_1$, -alkenyl($C_2$-$C_6$)—$Cy_1$, -alkynyl($C_2$-$C_6$)—$Cy_1$, —O-alkyl($C_1$-$C_6$)—$R_{10}$, —C(O)—$OR_9$, —O—C(O)—$R_9$, —C(O)—$NR_9R_9$', —$NR_9$—C(O)—$R_9$', —$NR_9$—C(O)—$OR_9$', -alkyl($C_1$-$C_6$)—$NR_9$—C(O)—$R_9$', —$SO_2$—$NR_9R_9$', —$SO_2$-alkyl($C_1$-$C_6$), or the substituents of the pair ($R_6$, $R_7$), when grafted onto two adjacent carbon atoms, form together with the carbon atoms carrying them an aromatic or non-aromatic ring composed of from 5 to 7 ring members, which may contain from 1 to 3 heteroatoms selected from oxygen, sulphur and nitrogen, it being understood that resulting ring may be substituted by a group selected from a linear or branched ($C_1$-$C_6$)alkyl group, —$NR_{11}R_{11}$', -alkyl($C_0$-$C_6$)—$Cy_1$, or an oxo, R$_8$ represents a linear or branched (C$_1$-C$_6$)alkyl group, a linear or branched (C$_2$-C$_6$)alkenyl group, a linear or branched (C$_2$-C$_6$)alkynyl group, —Cy$_3$, -alkyl(C$_1$-C$_6$)—Cy$_3$, -alkenyl(C$_2$-C$_6$)—Cy$_3$, -alkynyl(C$_2$-C$_6$)—Cy$_3$, —Cy$_3$-Cy$_4$, -alkynyl(C$_2$-C$_6$)—O—Cy$_3$, —Cy$_3$-alkyl(C$_0$-C$_6$)—O-alkyl(C$_0$-C$_6$)—Cy$_4$, a halogen atom, a cyano group, —C(O)—R$_{12}$, or —C(O)—NR$_{12}$R$_{12}$', R$_9$ and R$_9$' independently of one another represent a hydrogen atom, a linear or branched (C$_1$-C$_6$)alkyl group, -alkyl(C$_0$-C$_6$)—Cy$_1$, or the substituents of the pair (R$_9$, R$_9$') form together with the nitrogen atom carrying them an aromatic or non-aromatic ring composed of from 5 to 7 ring members, which may contain in addition to the nitrogen atom from 1 to 3 heteroatoms selected from oxygen, sulphur and nitrogen, it being understood that the nitrogen in question may be substituted by a group representing a hydrogen atom, or a linear or branched (C$_1$-C$_6$)alkyl group and it being understood that one or more of the carbon atoms of the possible substituents, may be deuterated, R$_{10}$ represents —Cy$_1$, —Cy$_1$-alkyl(C$_0$-C$_6$)—Cy$_2$, —Cy$_1$-alkyl(C$_0$-C$_6$)—O-alkyl(C$_0$-C$_6$)—Cy$_2$, —Cy$_1$-alkyl(C$_0$-C$_6$)—NR$_9$-alkyl(C$_0$-C$_6$)—Cy$_2$, —Cy$_1$-Cy$_2$-O-alkyl(C$_0$-C$_6$)—Cy$_5$, —C(O)—NR$_9$R$_9$', —NR$_9$R$_9$', —OR$_9$, —NR$_9$—C(O)—R$_9$', —O-alkyl(C$_1$-C$_6$)—OR$_9$, —SO$_2$—R$_9$, —C(O)—OR$_9$, or —NH—C(O)—NH—R$_9$, R$_{11}$, R$_{11}$', R$_{12}$ and R$_{12}$' independently of one another represent a hydrogen atom or an optionally substituted linear or branched (C$_1$-C$_6$)alkyl group, R$_{13}$ represents a hydrogen atom, a hydroxy group, or a hydroxy(C$_1$-C$_6$)alkyl group, R$_a$ represents a hydrogen atom or a linear or branched (C$_1$-C$_6$)alkyl group, R$_b$ represents a —O—C(O)—O—R$_c$ group, a —O—C(O)—NR$_c$R$_c$' group, or a —O—P(O)(OR$_c$)$_2$ group, R$_c$ and R$_c$' independently of one another represent a hydrogen atom, a linear or branched (C$_1$-C$_8$)alkyl group, a cycloalkyl group, a (C$_1$-C$_6$)alkoxy(C$_1$-C$_6$)alkyl group, a (C$_1$-C$_6$)alkoxycarbonyl(C$_1$-C$_6$)alkyl group, or the substituents of the pair (R$_c$, R$_c$') form together with the nitrogen atom carrying them a non-aromatic ring composed of from 5 to 7 ring members, which may contain in addition to the nitrogen atom from 1 to 3 heteroatoms selected from oxygen and nitrogen, it being understood that the nitrogen in question may be substituted by a group representing a linear or branched (C$_1$-C$_6$)alkyl group, Cy$_1$, Cy$_2$, Cy$_3$, Cy$_4$, Cy$_5$ and Cy$_6$ independently of one another, represent a cycloalkyl group, a heterocycloalkyl group, an aryl group or a heteroaryl group, n is an integer equal to 0 or 1, it being understood that:
"aryl" means a phenyl, naphthyl, biphenyl, indanyl or indenyl group,
"heteroaryl" means any mono- or bi-cyclic group composed of from 5 to 10 ring members, having at least one aromatic moiety and containing from 1 to 3 heteroatoms selected from oxygen, sulphur and nitrogen,
"cycloalkyl" means any mono- or bi-cyclic non-aromatic carbocyclic group containing from 3 to 10 ring members,
"heterocycloalkyl" means any mono- or bi-cyclic non-aromatic carbocyclic group containing from 3 to 10 ring members, and containing from 1 to 3 heteroatoms selected from oxygen, sulphur and nitrogen, which may include fused, bridged or spiro ring systems, it being possible for the aryl, heteroaryl, cycloalkyl and heterocycloalkyl groups so defined and the alkyl, alkenyl, alkynyl, alkoxy groups, to be substituted by from 1 to 4 groups selected from optionally substituted linear or branched (C$_1$-C$_6$)alkyl, optionally substituted linear or branched (C$_2$-C$_6$)alkenyl group, optionally substituted linear or branched (C$_2$-C$_6$)alkynyl group, optionally substituted linear or branched (C$_1$-C$_6$)alkoxy, optionally substituted (C$_1$-C$_6$)alkyl-S—, hydroxy, oxo (or N-oxide where appropriate), nitro, cyano, —C(O)—OR', —O—C(O)—R', —C(O)—NR'R", —NR'R", —(C=NR')—OR", linear or branched (C$_1$-C$_6$)polyhaloalkyl, trifluoromethoxy, or halogen, it being understood that R' and R" independently of one another represent a hydrogen atom or an optionally substituted linear or branched (C$_1$-C$_6$)alkyl group, and it being understood that one or more of the carbon atoms of the preceding possible substituents, may be deuterated, their enantiomers, diastereoisomers and atropisomers, and addition salts thereof with a pharmaceutically acceptable acid or base.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid etc.

Among the pharmaceutically acceptable bases there may be mentioned, without implying any limitation, sodium hydroxide, potassium hydroxide, triethylamine, tert-butylamine etc.

Advantageously, at least one of the groups selected from R$_2$, R$_3$, R$_4$ and R$_5$ does not represent a hydrogen atom.

More especially, compounds of formula (I) to which preference is given are compounds wherein n is an integer equal to 1.

In another embodiment of the invention, an advantageous possibility consists of compounds of formula (I-a):

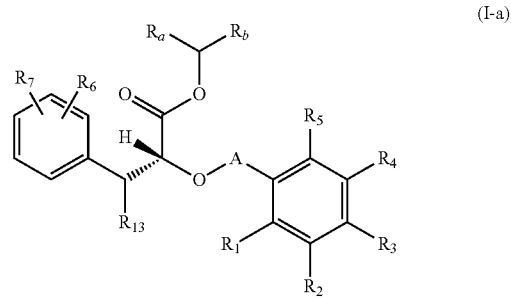

(I-a)

wherein R$_1$, R$_2$, R$_3$, R$_4$, R$_5$, R$_6$, R$_7$, R$_a$, R$_b$, R$_{13}$ and A are as defined for formula (I).

In the preferred compounds of the invention, R$_1$ represents a linear or branched (C$_1$-C$_6$)alkyl group or a halogen atom. More preferably, R$_1$ represents a methyl group, an ethyl group, a bromine atom or a chlorine atom.

Atropisomers are stereoisomers arising because of hindered rotation about a single bond, where energy differences due to steric strain or other contributors create a barrier to rotation that is high enough to allow for isolation of individual conformers. For compounds according to the invention, atropisomers are as follows:

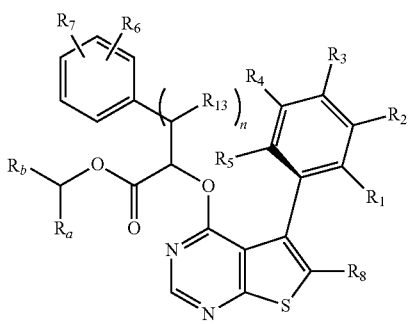

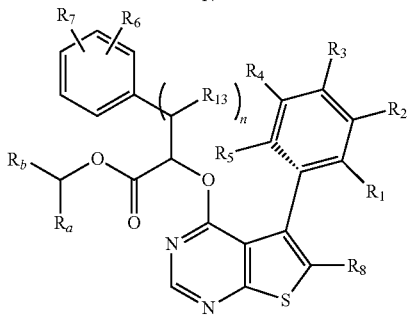

Preferred atropisomer is (5S$_a$).

Preferably, R$_{13}$ represents a hydrogen atom.

Advantageously, R$_2$ represents a halogen atom, a hydroxy group, a linear or branched (C$_1$-C$_6$)alkoxy group. More preferably, R$_2$ represents a methoxy group, a hydroxy group, a fluorine atom, a bromine atom or a chlorine atom. Even more preferably, R$_2$ represents a chlorine atom.

R$_3$ advantageously represents a hydrogen atom, a hydroxy group, a linear or branched (C$_1$-C$_6$)alkoxy group or —O-alkyl(C$_1$-C$_6$)—NR$_9$R$_9$'. Advantageously, R$_3$ represents —O-alkyl(C$_1$-C$_6$)—NR$_9$R$_9$'.

In some preferred embodiment of the invention,

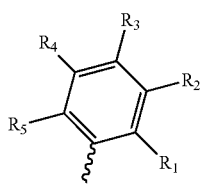

represents

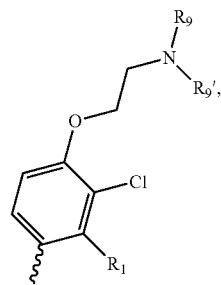

wherein R$_1$, R$_9$ and R$_9$' are as defined for formula (I).

In the preferred compounds of the invention,

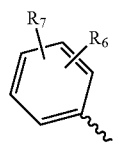

represents

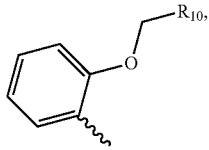

wherein R$_9$ and R$_9$' are as defined for formula (I).

R$_4$ and R$_5$ preferably represent a hydrogen atom.

In an advantageous embodiment, the substituents of the pair (R$_1$, R$_5$) are identical and the substituents of the pair (R$_2$, R$_4$) are identical. In the preferred compounds of the invention, the substituents of the pair (R$_1$, R$_5$) are identical and represent a (C$_1$-C$_6$)alkyl group, preferably a methyl group, whereas the substituents of the pair (R$_2$, R$_4$) are identical and represent a halogen atom, preferably a chlorine atom, or a hydrogen atom.

In another embodiment of the invention, R$_6$ represents an optionally substituted linear or branched (C$_1$-C$_6$)alkoxy group or a —O-alkyl(C$_1$-C$_6$)—R$_{10}$ group. Advantageously, R$_6$ represents a 2,2,2-trifluoroethoxy group, a methoxy group, a 2-methoxyethoxy group or a —O-alkyl(C$_1$-C$_6$)—R$_{10}$ group.

R$_7$ preferably represents a hydrogen atom.

In the preferred compounds of the invention, wherein R$_{10}$ is as defined for formula (I).

In another embodiment of the invention, an advantageous possibility consists of compounds of formula (I-b):

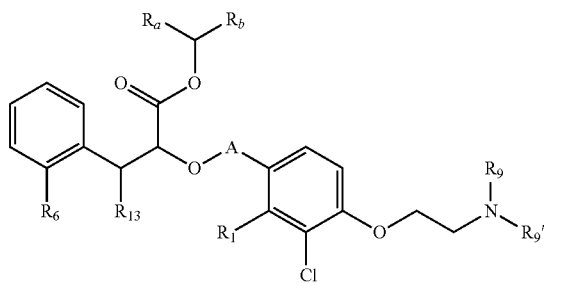

(I-b)

wherein $R_1$, $R_6$, $R_9$, $R_9'$, $R_a$, $R_b$, $R_{13}$ and A are as defined for formula (I).

In the preferred compounds of the invention, $R_8$ represents a linear or branched ($C_1$-$C_6$)alkyl group, a linear or branched ($C_2$-$C_6$)alkenyl group, a linear or branched ($C_2$-$C_6$)alkynyl group, an aryl group or a heteroaryl group. Advantageously, $R_8$ represents a linear or branched ($C_2$-$C_6$) alkynyl group, an aryl group or a heteroaryl group. More preferably, $R_8$ represents a prop-1-yn-1-yl group, a but-1-yn-1-yl group, a phenyl group or a furan-2-yl group. In a more preferred embodiment, $R_8$ represents a 4-(benzyloxy)phenyl group, a 4-(pyridin-4-ylmethoxy)phenyl group, a 4-phenylbut-1-yn-1-yl group, a 4-fluorophenyl group or a 5-fluorofuran-2-yl group. Even more preferentially, $R_8$ represents a 4-fluorophenyl group.

In the preferred compounds of the invention, $R_9$ and $R_9'$ independently of one another represent a linear or branched ($C_1$-$C_6$)alkyl group, or the substituents of the pair ($R_9$, $R_9'$) form together with the nitrogen atom carrying them a non-aromatic ring composed of from 5 to 7 ring members, which may contain in addition to the nitrogen atom from 1 to 3 heteroatoms selected from oxygen, sulphur and nitrogen, it being understood that the nitrogen in question may be substituted by a group representing a hydrogen atom or a linear or branched ($C_1$-$C_6$)alkyl group. More preferably, $R_9$ and $R_9'$ represent a methyl group, or the substituents of the pair ($R_9$, $R_9'$) form together a 4-methyl-piperazinyl group or a 4-ethyl-piperazinyl group. In a more preferred embodiment, the substituents of the pair ($R_9$, $R_9'$) form together a 4-methyl-piperazinyl group. In another preferred embodiment, $R_9$ and $R_9'$ represent a methyl group.

Advantageously, $R_{10}$ represents —$Cy_1$, —$Cy_1$-alkyl($C_0$-$C_6$)—O-alkyl($C_0$-$C_6$)—$Cy_2$ or —$Cy_1$-alkyl($C_0$-$C_6$)—$Cy_2$. More particularly, $R_{10}$ represents —$Cy_1$, —$Cy_1$-O—$CH_2$—$Cy_2$, or —$Cy_1$-$Cy_2$.

$Cy_1$ preferably represents a heteroaryl group, particularly, a pyrimidinyl group, a pyrazolyl group, a triazolyl group, a pyrazinyl group or a pyridinyl group. More preferably, $Cy_1$ represents a pyrimidin-4-yl group, a pyrazol-5-yl group, a triazol-5-yl group, a pyrazin-2-yl group or a pyridin-4-yl group. In the preferred compounds of the invention, $Cy_1$ represents a pyrimidin-4-yl group.

In another embodiment of the invention, $Cy_1$ represents a heteroaryl group which is substituted by an optionally substituted linear or branched ($C_1$-$C_6$)alkyl group, an optionally substituted linear or branched ($C_1$-$C_6$)alkoxy group, a —NR'R" group, or a linear or branched ($C_1$-$C_6$) polyhaloalkyl group, it being understood that R' and R" independently of one another represent a hydrogen atom or an optionally substituted linear or branched ($C_1$-$C_6$)alkyl group.

$Cy_2$ preferably represents a phenyl group, a pyridinyl group, a pyrazolyl group, a morpholinyl group, a furanyl group or a cyclopropyl group. More preferably, $Cy_2$ represents a phenyl group, a pyridin-2-yl group, a pyridin-3-yl group, a pyridin-4-yl group, a pyrazol-1-yl group, a morpholin-4-yl group, a furan-2-yl group or a cyclopropyl group. In the preferred compounds of the invention, $Cy_2$ represents a phenyl group.

Other compounds of the invention to which preference is given are those wherein $R_{10}$ represents —$Cy_1$-$Cy_2$ in which $Cy_1$ represents a pyrimidinyl group and $Cy_2$ represents a phenyl group, a pyridinyl group, a pyrazolyl group, a morpholinyl group, a furanyl group, or a cyclopropyl group. Even more preferentially, $R_{10}$ represents

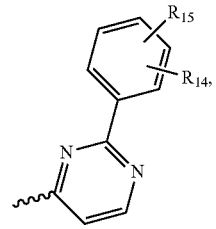

in which $R_{14}$ and $R_{15}$ independently of one another represent a hydrogen atom, an optionally substituted linear or branched ($C_1$-$C_6$)alkyl group, an optionally substituted linear or branched ($C_1$-$C_6$)alkoxy group, a hydroxy group, a linear or branched ($C_1$-$C_6$)polyhaloalkyl group, or a halogen atom. Preferred $R_{14}$ and $R_{15}$ groups are as follows: hydrogen; methyl; ethyl; methoxy; ethoxy; isopropoxy; methoxyethoxy; fluoro; hydroxy; trifluoromethyl. Advantageously, $R_{15}$ represents a hydrogen atom and $R_{14}$ is located at ortho position of the phenyl group.

More especially, compounds of formula (I) to which preference is given are compounds wherein $R_a$ represents a hydrogen atom or a methyl group.

Advantageously, $R_b$ represents a —O—C(O)—O—($C_1$-$C_8$)alkyl group; a —O—C(O)—O-cycloalkyl group; a —O—C(O)—$NR_cR_c'$ group, in which $R_c$ and $R_c'$ independently of one another represent a hydrogen atom, a linear or branched ($C_1$-$C_8$)alkyl group, a ($C_1$-$C_6$)alkoxy($C_1$-$C_6$)alkyl group, a ($C_1$-$C_6$)alkoxycarbonyl($C_1$-$C_6$)alkyl group, or the substituents of the pair ($R_c$, $R_c'$) form together with the nitrogen atom carrying them a non-aromatic ring composed of from 5 to 7 ring members, which may contain in addition to the nitrogen atom from 1 to 3 heteroatoms selected from oxygen and nitrogen; or a —O—P(O)(OH)$_2$ group.

Preferably, $R_a$ represents a methyl group and $R_b$ represents a group selected from —O—C(O)—O—$CH_3$; —O—C(O)—O—$CH_2CH_3$; —O—C(O)—O—$CH(CH_3)_2$; —O—C(O)—O—$C(CH_3)_3$; —O—C(O)—O-cyclopentyl; —O—C(O)—O—$C_8H_{17}$; —O—C(O)—N($CH_3$)$_2$; —O—C(O)—N($CH_2CH_3$)$_2$; —O—C(O)—N-morpholine; —O—C(O)—NH—($CH_2$)$_2$—$OCH_3$; —O—C(O)—N[($CH_2$)$_2$—$OCH_3$]$_2$; or —O—C(O)—N($CH_3$)($CH_2$—C(O)—$OCH_3$). More preferably, $R_a$ represents a methyl group and $R_b$ represents a group selected from —O—C(O)—O—$CH_2CH_3$ or —O—C(O)—N($CH_3$)$_2$.

Among the preferred compounds of the invention there may be mentioned:

1-[(methoxycarbonyl)oxy]ethyl (2R)-2-{[(5$S_a$)-5-{3-chloro-2-methyl-4-[2-(4-methylpiperazin-1-yl)ethoxy]phenyl}-6-(4-fluorophenyl)thieno[2,3-d]pyrimidin-4- yl]oxy}-3-(2-{[2-(2-methoxyphenyl)pyrimidin-4-yl]
methoxy}phenyl)propanoate;
1-[(ethoxycarbonyl)oxy]ethyl (2R)-2-{[(5S$_a$)-5-{3-chloro-2-methyl-4-[2-(4-methyl piperazin-1-yl)
ethoxy]phenyl}-6-(4-fluorophenyl)thieno[2,3-d]pyrimidin-4-yl]oxy}-3-(2-{[2-(2-methoxyphenyl)
pyrimidin-4-yl]methoxy}phenyl)propanoate;
1-{[(propan-2-yloxy)carbonyl]oxy}ethyl (2R)-2-{[(5S$_a$)-5-{3-chloro-2-methyl-4-[2-(4-methylpiperazin-1-yl)
ethoxy]phenyl}-6-(4-fluorophenyl)thieno[2,3-d]pyrimidin-4-yl]oxy}-3-(2-{[2-(2-methoxyphenyl)
pyrimidin-4-yl]methoxy}phenyl) propanoate;
1-[(tert-butoxycarbonyl)oxy]ethyl (2R)-2-{[(5S$_a$)-5-{3-chloro-2-methyl-4-[2-(4-methylpiperazin-1-yl)ethoxy]
phenyl}-6-(4-fluorophenyl)thieno[2,3-d]pyrimidin-4-yl]oxy}-3-(2-{[2-(2-methoxyphenyl)pyrimidin-4-yl]
methoxy}phenyl)propanoate;
1-{[(cyclopentyloxy)carbonyl]oxy}ethyl (2R)-2-{[(5S$_a$)-5-{3-chloro-2-methyl-4-[2-(4-methylpiperazin-1-yl)
ethoxy]phenyl}-6-(4-fluorophenyl)thieno[2,3-d]pyrimidin-4-yl]oxy}-3-(2-{[2-(2-methoxyphenyl)
pyrimidin-4-yl]methoxy}phenyl)propanoate;
1-{[(octyloxy)carbonyl]oxy}ethyl (2R)-2-{[(5S$_a$)-5-{3-chloro-2-methyl-4-[2-(4-methylpiperazin-1-yl)ethoxy]
phenyl}-6-(4-fluorophenyl)thieno[2,3-d]pyrimidin-4-yl]oxy}-3-(2-{[2-(2-methoxyphenyl)pyrimidin-4-yl]
methoxy}phenyl)propanoate;
1-[(dimethylcarbamoyl)oxy]ethyl (2R)-2-{[(5S$_a$)-5-{3-chloro-2-methyl-4-[2-(4-methylpiperazin-1-yl)ethoxy]
phenyl}-6-(4-fluorophenyl)thieno[2,3-d]pyrimidin-4-yl]oxy}-3-(2-{[2-(2-methoxyphenyl)pyrimidin-4-yl]
methoxy}phenyl)propanoate;
1-[(diethylcarbamoyl)oxy]ethyl (2R)-2-{[(5S$_a$)-5-{3-chloro-2-methyl-4-[2-(4-methylpiperazin-1-yl)ethoxy]
phenyl}-6-(4-fluorophenyl)thieno[2,3-d]pyrimidin-4-yl]oxy}-3-(2-{[2-(2-methoxyphenyl)pyrimidin-4-yl]
methoxy}phenyl)propanoate;
1-{[(2R)-2-{[(5S$_a$)-5-{3-chloro-2-methyl-4-[2-(4-methylpiperazin-1-yl)ethoxy]phenyl}-6-(4-fluorophenyl)
thieno[2,3-d]pyrimidin-4-yl]oxy}-3-(2-{[2-(2-methoxyphenyl)pyrimidin-4-yl]methoxy}phenyl)
propanoyl]oxy}ethyl morpholine-4-carboxylate;
1-{[(2-methoxyethyl)carbamoyl]oxy}ethyl (2R)-2-{[(5S$_a$-5-{3-chloro-2-methyl-4-[2-(4-methylpiperazin-1-yl)ethoxy]phenyl}-6-(4-fluorophenyl)thieno[2,3-d]
pyrimidin-4-yl]oxy}-3-(2-{[2-(2-methoxyphenyl)
pyrimidin-4-yl]methoxy}phenyl) propanoate;
1-{[bis(2-methoxyethyl)carbamoyl]oxy}ethyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]
pyrimidin-4-yl]oxy}-3-(2-{[2-(2-methoxyphenyl)
pyrimidin-4-yl]methoxy}phenyl)propanoate;
1-{[(2-methoxy-2-oxoethyl)(methyl)carbamoyl]
oxy}ethyl (2R)-2-{[(5S$_a$)-5-{3-chloro-2-methyl-4-[2-(4-methylpiperazin-1-yl)ethoxy]phenyl}-6-(4-fluoro phenyl)
thieno[2,3-d]pyrimidin-4-yl]oxy}3-(2-{[2-(2-methoxyphenyl)pyrimidin-4-yl]methoxy}phenyl)
propanoate;
(phosphonooxy)methyl (2R)-2-{[(5S$_a$)-5-{3-chloro-2-methyl-4-[2-(4-methyl piperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]
methoxy}phenyl)propanoate;
1-[(ethoxycarbonyl)oxy]ethyl (2)-2-{[5-{2,6-dimethyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)
propanoate;
1-[(ethoxycarbonyl)oxy]ethyl (2R)-2-{[5-{3,5-dichloro-2,6-dimethyl-4-[2-(4-methylpiperazin-1-yl)ethoxy]
phenyl}-6-(4-fluorophenyl)thieno[2,3-d]pyrimidin-4-yl]oxy}-3-(2-{[2-(2-methoxyphenyl)pyrimidin-4-yl]
methoxy}phenyl)propanoate;
1-[(dimethylcarbamoyl)oxy]ethyl (2R)-2-{[5-{2,6-dimethyl-4-[2-(4-methyl piperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]
methoxy}phenyl)propanoate;
1-[(dimethylcarbamoyl)oxy]ethyl (2R)-2-{[5-{3,5-dichloro-2,6-dimethyl-4-[2-(4-methylpiperazin-1-yl)
ethoxy]phenyl}-6-(4-fluorophenyl)thieno[2,3-d]pyrimidin-4-yl]oxy}-3-(2-{[2-(2-methoxyphenyl)
pyrimidin-4-yl]methoxy}phenyl)propanoate.

The invention relates also to a process for the preparation of compounds of formula (I), which process is characterised in that there is used as starting material the compound of formula (II):

(II)

wherein A is as defined for formula (I) in which 1 is linked to the chlorine atom and 2 is linked to the bromine atom, which compound of formula (II) is subjected to coupling with a compound of formula (III):

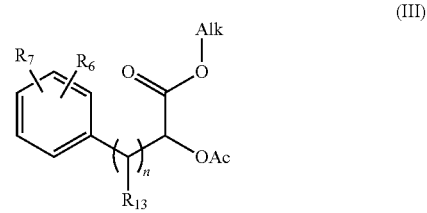

(III)

wherein $R_6$, $R_7$, $R_{13}$ and n are as defined for formula (I), and Alk represents an optionally substituted linear or branched $(C_1-C_6)$alkyl group, to yield the compound of formula (IV):

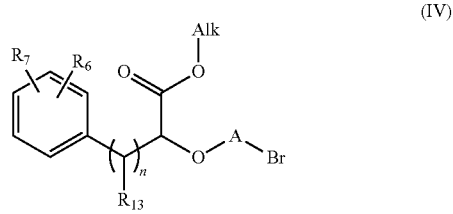

(IV)

wherein $R_6$, $R_7$, $R_{13}$, A and n are as defined for formula (I) and Alk is as defined before, compound of formula (IV) which is further subjected to coupling with compound of formula (V):

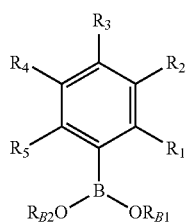

wherein $R_1$, $R_2$, $R_3$, $R_4$ and $R_5$ are as defined for formula (I), and $R_{B1}$ and $R_{B2}$ represent a hydrogen atom, a linear or branched ($C_1$-$C_6$) alkyl group, or $R_{B1}$ and $R_{B2}$ form with the oxygen carrying them an optionally methylated ring,
to yield the compound of formula (VI):

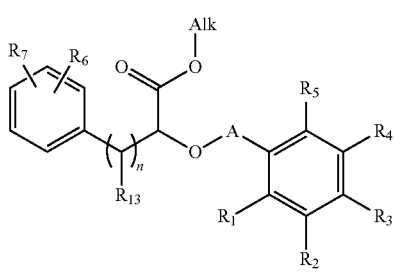

wherein $R_1$, $R_2$, $R_3$, $R_4$, $R_5$, $R_6$, $R_7$, $R_{13}$, A and n are as defined for formula (I) and Alk is as defined before,
the Alk—O—C(O)— ester function of which compound of formula (VI) is hydrolysed to yield the carboxylic acid (VII):

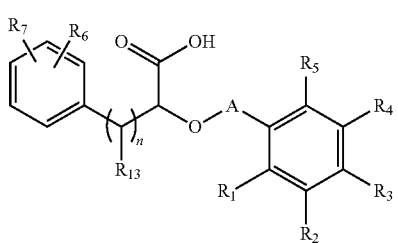

wherein $R_1$, $R_2$, $R_3$, $R_4$, $R_5$, $R_6$, $R_7$, $R_{13}$, A and n are as defined for formula (I),
which is subjected to coupling with a compound of formula (VIII):

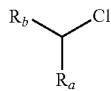

wherein $R_a$ and $R_b$ are as defined for formula (I),
to yield the compound of formula (I), which may be purified according to a conventional separation technique, which is converted, if desired, into its addition salts with a pharmaceutically acceptable acid or base and which is optionally separated into its isomers according to a conventional separation technique, it being understood that at any moment considered appropriate during the course of the process described above, some groups (hydroxy, amino . . . ) of the starting reagents or of the synthesis intermediates can be protected, subsequently deprotected and functionalized, as required by the synthesis.

The compounds of formulae (II), (III), (V) and (VIII) are either commercially available or can be obtained by the person skilled in the art using conventional chemical reactions described in the literature.

The invention relates also to compound of formula ($VI_A$), a particular case of compound of formula (VI):

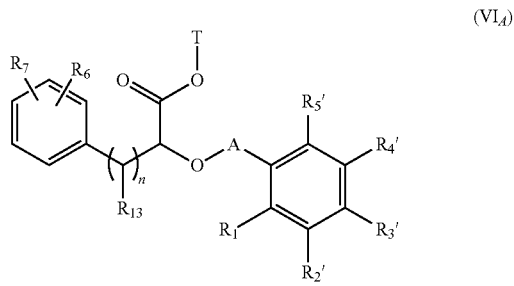

wherein:

$R_2'$, $R_3'$, $R_4'$ and $R_5'$ independently of one another represent a halogen atom, a linear or branched ($C_1$-$C_6$)alkyl group, a linear or branched ($C_2$-$C_6$)alkenyl group, a linear or branched ($C_2$-$C_6$)alkynyl group, a linear or branched ($C_1$-$C_6$)polyhaloalkyl, a hydroxy group, a hydroxy($C_1$-$C_6$)alkyl group, a linear or branched ($C_1$-$C_6$)alkoxy group, a —S—($C_1$-$C_6$)alkyl group, a cyano group, a nitro group, -alkyl($C_0$-$C_6$)—$NR_9R_9'$, —O-alkyl($C_1$-$C_6$)—$NR_9R_9'$, —O-alkyl($C_1$-$C_6$)—$R_{10}$, —C(O)—$OR_9$, —O—C(O)—$R_9$, —C(O)—$NR_9R_9'$, —$NR_9$—C(O)—$R_9'$, —$NR_9$—C(O)—$OR_9'$, -alkyl($C_1$-$C_6$)—$NR_9$—C(O)—$R_9'$, —$SO_2$—$NR_9R_9'$, —$SO_2$-alkyl($C_1$-$C_6$), T represents a ($C_1$-$C_6$)alkyl group, a ($C_1$-$C_6$)carbonyloxy ($C_1$-$C_6$)alkyl group or a di($C_1$-$C_6$)alkylaminocarbonyl ($C_1$-$C_6$)alkyl group, $R_1$, $R_6$, $R_7$, $R_{13}$, A and n are as defined for formula (I), its enantiomers, diastereoisomers and atropisomers, and addition salts thereof with a pharmaceutically acceptable acid or base,
as synthesis intermediate but also as compound for use as pro-apoptotic agents.

The invention relates to compound of formula ($VII_A$), a particular case of compound of formula (VII):

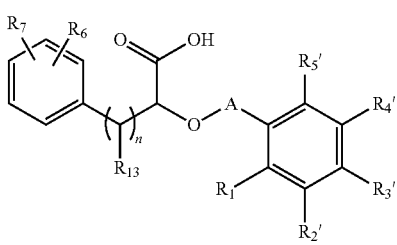

wherein:
R$_2$', R$_3$', R$_4$' and R$_5$' independently of one another represent a halogen atom, a linear or branched (C$_1$-C$_6$)alkyl group, a linear or branched (C$_2$-C$_6$)alkenyl group, a linear or branched (C$_2$-C$_6$)alkynyl group, a linear or branched (C$_1$-C$_6$)polyhaloalkyl, a hydroxy group, a hydroxy(C$_1$-C$_6$)alkyl group, a linear or branched (C$_1$-C$_6$)alkoxy group, a —S—(C$_1$-C$_6$)alkyl group, a cyano group, a nitro group, -alkyl(C$_0$-C$_6$)—NR$_9$R$_9$', —O-alkyl(C$_1$-C$_6$)—NR$_9$R$_9$', —O-alkyl(C$_1$-C$_6$)—R$_{10}$, —C(O)—OR$_9$, —O—C(O)—R$_9$, —C(O)—NR$_9$R$_9$', —NR$_9$—C(O)—R$_9$', —NR$_9$—C(O)—OR$_9$', -alkyl(C$_1$-C$_6$)—NR$_9$—C(O)—R$_9$', —SO$_2$—NR$_9$R$_9$', —SO$_2$-alkyl(C$_1$-C$_6$), R$_1$, R$_6$, R$_7$, R$_{13}$, A and n are as defined for formula (I), its enantiomers, diastereoisomers and atropisomers, and addition salts thereof with a pharmaceutically acceptable acid or base,
as synthesis intermediate but also as compound for use as pro-apoptotic agents.

Advantageously, for compounds of formula (VI$_A$) and (VII$_A$), the substituents of the pair (R$_1$, R$_5$') are identical and the substituents of the pair (R$_2$', R$_4$') are identical.

Preferred compound of formula (VII$_A$) is (2R)-2-{[5-{3,5-dichloro-2,6-dimethyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid.

The invention relates also to compound of formula (VI$_B$), a particular case of compound of formula (VI):

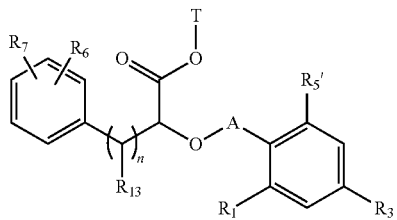

(VI$_B$)

wherein:
R$_5$' represents a halogen atom, a linear or branched (C$_1$-C$_6$)alkyl group, a linear or branched (C$_2$-C$_6$)alkenyl group, a linear or branched (C$_2$-C$_6$)alkynyl group, a linear or branched (C$_1$-C$_6$)polyhaloalkyl, a hydroxy group, a hydroxy(C$_1$-C$_6$)alkyl group, a linear or branched (C$_1$-C$_6$)alkoxy group, a —S—(C$_1$-C$_6$)alkyl group, a cyano group, a nitro group, -alkyl(C$_0$-C$_6$)—NR$_9$R$_9$', —O-alkyl(C$_1$-C$_6$)—NR$_9$R$_9$', —O-alkyl(C$_1$-C$_6$)—R$_{10}$, —C(O)—OR$_9$, —O—C(O)—R$_9$, —C(O)—NR$_9$R$_9$', —NR$_9$—C(O)—R$_9$', —NR$_9$—C(O)—OR$_9$', -alkyl(C$_1$-C$_6$)—NR$_9$—C(O)—R$_9$', —SO$_2$—NR$_9$R$_9$', —SO$_2$-alkyl(C$_1$-C$_6$), T represents a (C$_1$-C$_6$)alkyl group, a (C$_1$-C$_6$)carbonyloxy (C$_1$-C$_6$)alkyl group or a di(C$_1$-C$_6$)alkylaminocarbonyl (C$_1$-C$_6$)alkyl group, R$_1$, R$_3$, R$_6$, R$_7$, R$_{13}$, A and n are as defined for formula (I), and wherein the substituents of the pair (R$_1$, R$_5$') are identical,
its enantiomers, diastereoisomers and atropisomers, and addition salts thereof with a pharmaceutically acceptable acid or base,
as synthesis intermediate but also as compound for use as pro-apoptotic agents.

The invention relates to compound of formula (VII$_B$), a particular case of compound of formula (VII):

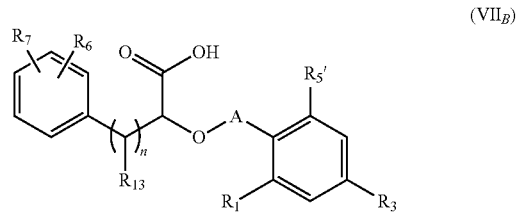

(VII$_B$)

wherein:
R$_5$' represents a halogen atom, a linear or branched (C$_1$-C$_6$)alkyl group, a linear or branched (C$_2$-C$_6$)alkenyl group, a linear or branched (C$_2$-C$_6$)alkynyl group, a linear or branched (C$_1$-C$_6$)polyhaloalkyl, a hydroxy group, a hydroxy(C$_1$-C$_6$)alkyl group, a linear or branched (C$_1$-C$_6$)alkoxy group, a —S—(C$_1$-C$_6$)alkyl group, a cyano group, a nitro group, -alkyl(C$_0$-C$_6$)—NR$_9$R$_9$', —O-alkyl(C$_1$-C$_6$)—NR$_9$R$_9$', —O-alkyl(C$_1$-C$_6$)—R$_{10}$, —C(O)—OR$_9$, —O—C(O)—R$_9$, —C(O)—NR$_9$R$_9$', —NR$_9$—C(O)—R$_9$', —NR$_9$—C(O)—OR$_9$', -alkyl(C$_1$-C$_6$)—NR$_9$—C(O)—R$_9$', —SO$_2$—NR$_9$R$_9$', —SO$_2$-alkyl(C$_1$-C$_6$), R$_1$, R$_3$, R$_6$, R$_7$, R$_{13}$, A and n are as defined for formula (I), and wherein the substituents of the pair (R$_1$, R$_5$') are identical,
its enantiomers, diastereoisomers and atropisomers, and addition salts thereof with a pharmaceutically acceptable acid or base,
as synthesis intermediate but also as compound for use as pro-apoptotic agents.

Preferred compounds of formula (VII$_B$) is (2R)-2-{[5-{2,6-dimethyl-4-[2-(4-methyl piperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid.

Pharmacological study of the compounds of the invention has shown that they have pro-apoptotic properties. The ability to reactivate the apoptotic process in cancerous cells is of major therapeutic interest in the treatment of cancers and of immune and auto-immune diseases.

More especially, the compounds according to the invention will be useful in the treatment of chemo- or radio-resistant cancers.

Among the cancer treatments envisaged there may be mentioned, without implying any limitation, treatment of cancers of the bladder, brain, breast and uterus, chronic lymphoid leukaemias, cancer of the colon, oesophagus and liver, lymphoblastic leukaemias, acute myeloid leukaemias, lymphomas, melanomas, malignant haemopathies, myelomas, ovarian cancer, non-small-cell lung cancer, prostate cancer, pancreatic cancer and small-cell lung cancer.

The present invention relates also to pharmaceutical compositions comprising at least one compounds of formulae (I), (VI$_A$), (VI$_B$), (VII$_A$) or (VII$_B$) in combination with one or more pharmaceutically acceptable excipients.

Among the pharmaceutical compositions according to the invention there may be mentioned more especially those that are suitable for oral, parenteral, nasal, per- or trans-cutaneous, rectal, perlingual, ocular or respiratory administration, especially tablets or dragées, sublingual tablets, sachets, paquets, capsules, glossettes, lozenges, suppositories, creams, ointments, dermal gels, and drinkable or injectable ampoules.

The dosage varies according to the sex, age and weight of the patient, the administration route, the nature of the therapeutic indication, or of any associated treatments, and ranges from 0.01 mg to 1 g per 24 hours in one or more administrations.

Furthermore, the present invention relates also to the combination of a compound of formulae (I), (VI$_A$), (VI$_B$), (VII$_A$) or (VII$_B$) with an anticancer agent selected from genotoxic agents, mitotic poisons, anti-metabolites, proteasome inhibitors, kinase inhibitors and antibodies, and also to pharmaceutical compositions comprising that type of combination and their use in the manufacture of medicaments for use in the treatment of cancer.

Advantageously, the present invention relates to the combination of a compound of formulae (I), (VI$_A$), (VI$_B$), (VII$_A$) or (VII$_B$) with an EGFR inhibitor, and also to pharmaceutical compositions comprising that type of combination.

In another embodiment, the present invention relates to the combination of a compound of formulae (I), (VI$_A$), (VI$_B$), (VII$_A$) or (VII$_B$) with a mTOR/PI3K inhibitor, and also to pharmaceutical compositions comprising that type of combination.

In a preferred embodiment, the present invention relates to the combination of a compound of formulae (I), (VI$_A$), (VI$_B$), (VII$_A$) or (VII$_B$) with a MEK inhibitor, and also to pharmaceutical compositions comprising that type of combination.

Preferably, the present invention relates to the combination of a compound of formulae (I), (VI$_A$), (VI$_B$), (VII$_A$) or (VII$_B$) with a HER2 inhibitor, and also to pharmaceutical compositions comprising that type of combination.

Advantageously, the present invention relates to the combination of a compound of formulae (I), (VI$_A$), (VI$_B$), (VII$_A$) or (VII$_B$) with a RAF inhibitor, and also to pharmaceutical compositions comprising that type of combination.

In another embodiment, the present invention relates to the combination of a compound of formulae (I), (VI$_A$), (VI$_B$), (VII$_A$) or (VII$_B$) with a EGFR/HER2 inhibitor, and also to pharmaceutical compositions comprising that type of combination.

In a preferred embodiment, the present invention relates to the combination of a compound of formulae (I), (VI$_A$), (VI$_B$), (VII$_A$) or (VII$_B$) with a taxane, and also to pharmaceutical compositions comprising that type of combination.

In another embodiment, the present invention relates to the combination of a compound of formulae (I), (VI$_A$), (VI$_B$), (VII$_A$) or (VII$_B$) with a proteasome inhibitor, an immunomodulator or an alkylating agent, and also to pharmaceutical compositions comprising that type of combination.

The combination of a compound of formulae (I), (VI$_A$), (VI$_B$), (VII$_A$) or (VII$_B$) with an anticancer agent may be administered simultaneously or sequentially. The administration route is preferably the oral route, and the corresponding pharmaceutical compositions may allow the instantaneous or delayed release of the active ingredients. The compounds of the combination may moreover be administered in the form of two separate pharmaceutical compositions, each containing one of the active ingredients, or in the form of a single pharmaceutical composition, in which the active ingredients are in admixture.

The compounds of the invention may also be used in combination with radiotherapy in the treatment of cancer.

Finally, the compounds of the invention may be linked to monoclonal antibodies or fragments thereof or linked to scaffold proteins that can be related or not to monoclonal antibodies.

Antibody fragments must be understood as fragments of Fv, scFv, Fab, F(ab')2, F(ab'), scFv-Fc type or diabodies, which generally have the same specificity of binding as the antibody from which they are descended. According to the present invention, antibody fragments of the invention can be obtained starting from antibodies by methods such as digestion by enzymes, such as pepsin or papain, and/or by cleavage of the disulfide bridges by chemical reduction. In another manner, the antibody fragments comprised in the present invention can be obtained by techniques of genetic recombination likewise well known to the person skilled in the art or else by peptide synthesis by means of, for example, automatic peptide synthesizers such as those supplied by the company Applied Biosystems, etc.

Scaffold proteins that can be related or not to monoclonal antibodies are understood to mean a protein that contains or not an immunoglobulin fold and that yields a binding capacity similar to a monoclonal antibody. The man skilled in the art knows how to select the protein scaffold. More particularly, it is known that, to be selected, such a scaffold should display several features as follow (Skerra A., J. Mol. Recogn. 2000, 13, 167-187): phylogenetically good conservation, robust architecture with a well-known three-dimensional molecular organization (such as, for example, crystallography or NMR), small size, no or only a low degree of post-translational modifications, easy to produce, express and purify. Such a protein scaffold can be, but without limitation, a structure selected from the group consisting in fibronectin and preferentially the tenth fibronectin type III domain (FNfn10), lipocalin, anticalin (Skerra A., J. Biotechnol. 2001, 74(4), 257-75), the protein Z derivative from the domain B of staphylococcal protein A, thioredoxin A or any protein with a repeated domain such as an "ankyrin repeat" (Kohl et al., PNAS 2003, 100(4), 1700-1705), "armadillo repeat", "leucine-rich repeat" or "tetratricopeptide repeat". There could also be mentioned a scaffold derivative from toxins (such as, for example, scorpion, insect, plant or mollusc toxins) or protein inhibitors of neuronal nitric oxide synthase (PIN).

The following Preparations and Examples illustrate the invention but do not limit it in any way.

General Procedures

All reagents obtained from commercial sources were used without further purification. Anhydrous solvents were obtained from commercial sources and used without further drying.

Flash chromatography was performed on ISCO Combi-Flash Rf 200i with pre-packed silica-gel cartridges (RediSep®R$_f$ Gold High Performance).

Thin layer chromatography was conducted with 5×10 cm plates coated with Merck Type 60 F254 silica-gel.

Microwave heating was performed in an Anton Parr MonoWave or CEM Discover® instrument.

Preparative HPLC purifications were performed on an Armen Spot Liquid Chromatography system with a Gemini-NX® 10 μM C18, 250 mm×50 mm i.d. column running at a flow rate of 118 mL min$^{-1}$ with UV diode array detection (210-400 nm) using 25 mM aqueous NH$_4$HCO$_3$ solution and MeCN as eluents unless specified otherwise.

Analytical LC-MS: The compounds of the present invention were characterized by high performance liquid chromatography-mass spectroscopy (HPLC-MS) on Agilent HP1200 with Agilent 6140 quadrupole LC/MS, operating in positive or negative ion electrospray ionisation mode. Molecular weight scan range is 100 to 1350. Parallel UV detection was done at 210 nm and 254 nm. Samples were supplied as a 1 mM solution in ACN, or in THF/H$_2$O (1:1) with 5 µL loop injection. LCMS analyses were performed on two instruments, one of which was operated with basic, and the other with acidic eluents. Basic LCMS: Gemini-NX, 3 µm, C18, 50 mm×3.00 mm i.d. column at 23° C., at a flow rate of 1 mL min$^{-1}$ using 5 mM ammonium bicarbonate (Solvent A) and acetonitrile (Solvent B) with a gradient starting from 100% Solvent A and finishing at 100% Solvent B over various/certain duration of time.

Acidic LCMS: ZORBAX Eclipse XDB-C18, 1.8 µm, 50 mm×4.6 mm i.d. column at 40° C., at a flow rate of 1 mL·min$^{-1}$ using 0.02% v/v aqueous formic acid (Solvent A) and 0.02% v/v formic acid in acetonitrile (Solvent B) with a gradient starting from 100% Solvent A and finishing at 100% Solvent B over various/certain duration of time.

$^1$H-NMR measurements were performed on Bruker Avance III 500 MHz spectrometer and Bruker Avance III 400 MHz spectrometer, using DMSO-d$_6$ or CDCl$_3$ as solvent. $^1$H NMR data is in the form of delta values, given in part per million (ppm), using the residual peak of the solvent (2.50 ppm for DMSO-d$_6$ and 7.26 ppm for CDCl$_3$) as internal standard. Splitting patterns are designated as: s (singlet), d (doublet), t (triplet), q (quartet), quint (quintet), m (multiplet), br s (broad singlet), dd (doublet of doublets), td (triplet of doublets), dt (doublet of triplets), ddd (doublet of doublets).

Combination gas chromatography and low resolution mass spectrometry were performed on Agilent 6850 gas chromatograph and Agilent 5975C mass spectrometer using 15 m×0.25 mm column with 0.25 µm HP-5MS coating and helium as carrier gas. Ion source: EI$^+$, 70 eV, 230° C., quadrupole: 150° C., interface: 300° C.

HRMS were determined on a Shimadzu IT-TOF, ion source temperature 200° C., ESI +/−, ionization voltage: (+−)4.5 kV. Mass resolution min. 10000.

Elementary analyses were performed on a Thermo Flash EA 1112 Elemental Analyzer.

LIST OF ABBREVIATIONS

| Abbreviation | Name |
| --- | --- |
| Ac | acetyl |
| AIBN | 2-[(1-cyano-1-methyl-ethyl)azo]-2-methyl-propanenitrile |
| AtaPhos | bis(di-tert-butyl(4-dimethylaminophenyl)phosphine)dichloropalladium(II) |
| DCM | dichloromethane |
| DIPA | diisopropylamine |
| DMF | dimethylformamide |
| DMSO | dimethyl sulfoxide |
| eq. | equivalent |
| Et | ethyl |
| HMDS | hexamethyldisilazane |
| $^i$Pr | isopropyl |
| Me | methyl |
| MeCN, ACN | acetonitrile |
| NBS | N-bromosuccinimide |
| NCS | N-chlorosuccinimide |
| $^n$Bu | n-butyl |
| Ph | phenyl |
| r.t. | room temperature |
| $^t$Bu | tert-butyl |
| tBuXPhos | 2-di(tert-butylphosphino)-2',4',6'-triisopropylbiphenyl |
| TFA | trifluoroacetic acid |
| THF | tetrahydrofurane |

General Procedure I:

Step A 1 eq. of the appropriate alcohol and 1.2 eq. pyridine were dissolved in DCM (1.2 mL/mmol). 1.05 eq. 1-chloroethyl chloroformate was slowly added at −78° C. under nitrogen and the reaction mixture was stirred at −78° C. for 3 hours. The cold mixture was filtered and the filtrate was concentrated under reduced pressure. The crude product was used without further purification.

Step B 1 eq. Preparation 12, Preparation 13 or Preparation 14 was dissolved in DMF (20 ml/mmol) under nitrogen. 6.7 eq. Cs$_2$CO$_3$ and 8 eq. of the 1-chloroethyl carbonate reagent was added. The reaction mixture was stirred at room temperature until no further conversion was observed. The mixture was diluted with brine and it was extracted with DCM, dried with Na$_2$SO$_4$, filtered and concentrated under reduced pressure. The crude product was purified via preparative reverse phase chromatography using 5 mM aqueous NH$_4$HCO$_3$ solution and acetonitrile as eluents to obtain the appropriate carbonate derivative as a mixture of stereoisomers.

General Procedure II:

Step A 1.05 eq. amine reagent and 1.15 eq. pyridine were dissolved in 1.3 mL/mmol DCM, then 1 eq. 1-chloroethyl chloroformate was added at −78° C. under nitrogen. The reaction mixture was stirred at −78° C. until no further conversion was observed. The cold mixture was filtered; the filtrate was concentrated under reduced pressure (30 mbar) using a 30° C. bath. The crude product was used within 3 hours without further purification.

Step B 1 eq. Preparation 12, Preparation 13 or Preparation 14 was dissolved in 20 ml/mmol DMF under nitrogen. 10 eq. Cs$_2$CO$_3$, then 8 eq carbamate reagent (0.8 M solution of crude product from Step A in DMF) was added. The reaction mixture was stirred at r.t. until no further conversion was achieved. The mixture was diluted with brine and it was extracted several times with ethylacetate. Combined organic layer was dried over MgSO$_4$, filtered and concentrated under reduced pressure and purified via preparative reversed phase chromatography using 5 mM aqueous NH$_4$HCO$_3$ solution and acetonitrile as eluents to obtain the carbamate derivative.

Preparation 1: 5-Bromo-4-chloro-6-iodo-thieno[2,3-d]pyrimidine

Step A: 6-Iodo-3H-thieno[2,3-d]pyrimidin-4-one

A 2 L round bottomed flask equipped with mechanical stirrer, thermometer and reflux condenser was charged with the solution of 433 mL acetic acid, 13 mL sulfuric acid and 87 mL water. 69.3 g 3H-thieno[2,3-d]pyrimidin-4-one (0.46 mol), 51.9 g periodic acid (0.23 mol) and 104 g iodine (0.41 mol) were added to the stirred solution heated to 60° C. for 1 hour. The resulting suspension was cooled to r.t., filtered off, washed with a mixture of acetic acid and water (5:1) and then with diethyl ether. The resulting beige crystalline solid was air dried. $^1$H NMR (500 MHz, DMSO-d$_6$): 12.57 (br s, 1H), 8.09 (s, 1H), 7.65 (s, 1H)

Step B: 4-Chloro-6-iodo-thieno[2,3-d]pyrimidine

A 1 L round bottomed flask equipped with mechanical stirrer, thermometer, reflux condenser and a CaCl$_2$-tube was charged with 113 mL phosphorous oxychloride and 35 mL N,N-dimethyl aniline (0.29 mol). 75.54 g 6-iodo-3H-thieno[2,3-d]pyrimidin-4-one (0.27 mol) was added to the mixture in portions during 5 minutes. The reaction mixture was stirred at 105° C. for 1 hour. The resulting suspension was cooled to 10° C., filtered and washed with hexane. The crude product was added to ice water and stirred for 10 minutes, filtered off, washed with cold water, diethyl ether and air dried. Beige crystalline solid was obtained. $^1$H NMR (400 MHz, DMSO-d$_6$): 8.89 (s, 1H), 7.98 (s, 1H)

Step C: Preparation 1

A 2 L round bottomed flask equipped with mechanical stirrer, thermometer and a bubbler was charged with 600 mL acetonitrile. 84.9 g 4-chloro-6-iodo-thieno[2,3-d]pyrimidine (0.29 mol), 50.9 g NBS (0.29 mol) and 8.5 mL tetrafluoroboric acid diethyl ether complex were added. The reaction mixture was stirred at r.t. for 16 hours. Further 22.9 g (0.12 mol) NBS was added to the mixture in three portions. After cooling the suspension to 0° C. and stirring for further 1 hour the precipitate was filtered off, washed with acetonitrile and air dried. Preparation 1 was obtained as beige crystalline solid. $^1$H NMR (500 MHz, DMSO-d$_6$): 8.88 (s, 1H)

Preparation 2: 5-Bromo-4-chloro-6-(4-fluorophenyl)thieno[2,3-d]pyrimidine 75.08 g Preparation 1 (200 mmol), 53.63 g 2-(4-fluorophenyl)-4,4,5,5-tetramethyl-1,3,2-dioxaborolane (240 mmol), 130 g cesium carbonate (400 mmol), 2.245 g Pd(OAc)$_2$ (10 mmol) and 8.50 g $^t$BuX-Phos (20 mmol) were placed in a 2 L flask. 600 mL THF and 200 mL water were added, and then stirred overnight at 70° C. under argon atmosphere. THF was evaporated, and then the product was collected by filtration. Crude product was sonicated in 250 mL acetonitrile and filtered again. Then Preparation 2 was crystallized from EtOH/THF (2:1). $^1$H NMR (400 MHz, DMSO-d$_6$): 9.02 (s, 1H), 7.80-7.77 (m, 2H), 7.47-7.43 (m, 2H)

Preparation 3: Ethyl (2R)-2-acetoxy-3-(2-hydroxyphenyl)propanoate

Step A: [2-(Bromomethyl)phenyl]acetate 60.07 g 2-methylphenyl acetate (400 mmol) and 106.8 g NBS (600 mmol) were placed in a 1 L flask. 500 mL cyclohexane was added, and then with intensive stirring 3.284 g AIBN (20 mmol) was added over 30 minutes. The mixture was stirred at 80° C. until no further conversion was observed, then cooled to r.t. The precipitate was filtered off and washed with cyclohexane. The mother liquor was concentrated under reduced pressure, and the crude product was used in Step B without further purification.

Step B: Preparation 3

23.10 g anhydrous LiCl (545 mmol) and 65.36 g anhydrous ZnCl$_2$ (479.6 mmol) were placed in a 2 L flask, then dried at 160° C. under 0.1 mmHg for 1 hour. After cooling to r.t. under argon atmosphere, 26.49 g magnesium turnings (1090 mmol) and 1 L dry pre-cooled (0° C.) THF were added. The resulting mixture was immersed into an ice-bath, and then stirred for 30 minutes.

100 g [2-(bromomethyl)phenyl]acetate—crude product from Step A—(~436 mmol) was dissolved in 120 mL dry THF and was added to the precooled inorganics over 15 minutes. After addition of the reagent the resulting mixture was stirred for 45 minutes while keeping the temperature between 0-5° C. To the mixture 64.82 mL ethyl 2-oxoacetate (654 mmol, 50% in toluene) was added over 5 minutes and the resulting mixture was stirred for another 15 minutes.

From the mixture the remaining inorganics were removed by filtration, and then 500 mL MeOH was added to the filtrate. This mixture was stirred until the intramolecular acetyl group migration from the phenolic oxygen to the alkyl oxygen was completed. To the mixture 30 mL acetic acid was added then the volatiles were evaporated under reduced pressure. To the residue 350 mL water was added and it was extracted with EtOAc. The combined organic layers were washed with saturated NaHCO$_3$ and with brine, and then dried over MgSO$_4$, filtered and evaporated under reduced pressure. To the residue 100 mL hexane was added and it was stirred for 30 minutes at 0° C. The formed white crystals were collected by filtration and washed with hexane yielding enantiomers which were separated via chiral chromatography.

Column: OD; Eluents: heptane/EtOH; the (S)-enantiomer eluting earlier was collected with 99.8% ee and the (R)-enantiomer eluting later was collected as Preparation 3 with 99.9% ee.

$^1$H NMR (500 MHz, DMSO-d$_6$) δ 9.53 (s, 1H), 7.06 (t, 1H), 7.04 (d, 1H), 6.79 (d, 1H), 6.71 (t, 1H), 5.10 (dd, 1H), 4.05 (q, 2H), 3.06 (dd, 1H), 2.94 (dd, 1H), 2.00 (s, 3H), 1.09 (t, 3H)

Preparation 4: Ethyl (2R)-2-hydroxy-3-(2-tetrahydropyran-2-yloxyphenyl)propanoate Step A: Ethyl (2R)-2-acetoxy-3-(2-tetrahydropyran-2-yloxyphenyl)propanoate 103.3 g Preparation 3 (409 mmol) was dissolved in 280 mL 3,4-dihydro-2H-pyran. 300 mg para-toluenesulfonic acid monohydrate was added and the mixture was stirred until no further conversion was observed. Then it was diluted with 1 L ethyl acetate, washed with 200 mL saturated NaHCO$_3$ solution, then with 200 mL water. Combined organic layers were dried over Na$_2$SO$_4$, filtered and concentrated. Then it was purified via flash chromatography using heptane/EtOAc.

Step B: Preparation 4

137.57 g ethyl (2R)-2-acetoxy-3-(2-tetrahydropyran-2-yloxyphenyl)propanoate (409 mmol) was dissolved in 600 mL ethanol, then 20 mL sodium ethoxide solution (1M in ethanol) was added and it was stirred until no further conversion was observed. The mixture was concentrated to half of its volume, then 300 mL water and 300 mL brine was added, and it was extracted with ethyl acetate. The combined organics were dried over sodium sulfate, filtered and concentrated. The enantiopurity of the starting material was conserved. $^1$H NMR (500 MHz, DMSO-d$_6$, 1:1 mixture of diastereomers) δ 7.16 (t, 1H), 7.13 (d, 1H), 7.04 (d, 1H), 6.87 (t, 1H), 5.51-5.47 (m, 1H), 4.27 (m, 1H), 4.04-4.02 (q, 2H), 3.73-3.56 (m, 2H), 3.06-3.04-2.74-2.71 (dd, 2H), 1.95-1.64 (m, 2H), 1.79 (m, 2H), 1.65-1.50 (m, 2H), 1.12-1.10 (t, 3H)

Preparation 5: Ethyl (2R)-2-[5-bromo-6-(4-fluorophenyl)thieno[2,3-d]pyrimidin-4-yl]oxy-3-(2-tetrahydropyran-2-yloxyphenyl)propanoate 48.45 g Preparation 2 (141 mmol), 45.63 g Preparation 4 (155 mmol) and 137.8 g Cs$_2$CO$_3$ (423 mmol) were placed in a 2 L flask. 1.4 L tert-butanol was added and the mixture was stirred at 70° C. under $N_2$ until no further conversion was observed. Approximately 1 L solvent was evaporated under reduced pressure, then it was diluted with water, the pH was set to 8 with 2M HCl, and then it was extracted with DCM. The combined organic layers were dried over $Na_2SO_4$, filtered and concentrated under reduced pressure. The crude product was purified via flash chromatography using heptane and EtOAc as eluents to obtain Preparation 5 as a mixture of diastereoisomers.

$^1$H NMR (500 MHz, DMSO-$d_6$): 8.67-8.66 (s, 1H), 7.75 (m, 2H), 7.43 (dm, 1H), 7.41 (m, 2H), 7.19 (m, 1H), 7.08-7.06 (dm, 1H), 6.89 (m, 1H), 5.87-5.70 (m, 1H), 5.60-5.55 (m, 1H), 4.23-4.08 (m, 2H), 3.80-3.48 (m, 2H), 3.52-3.49 (dd, 1H), 3.19-3.17 (dd, 1H), 2.09-1.49 (m, 6H), 1.15-1.10 (t, 3H)

HRMS calculated for $C_{28}H_{36}BrFN_2O_5S$: 600.0730, found: 601.0809/601.0798 (M+H)

Preparation 6: 2-Chloro-3-methyl-4-(4,4,5,5-tetramethyl-1,3,2-dioxaborolan-2-yl)phenol Step A: (4-Bromo-2-chloro-phenoxy)-trimethyl-silane 20.8 g 4-bromo-2-chloro-phenol (100 mmol) was dissolved in 150 mL dry THF then 24.2 g HMDS (150 mmol) was added. The reaction mixture was stirred at 85° C. under argon atmosphere for 1.5 hours then concentrated under reduced pressure resulting in the product used without further purification. $^1$H NMR (200 MHz, CDCl$_3$): 7.49 (d, 1H), 7.23 (dd, 1H), 6.75 (d, 1H), 0.26 (s, 9H)

Step B: 4-Bromo-2-chloro-3-methyl-phenol 48 mL ″BuLi solution in hexanes (2.5 M, 120 mmol) was added dropwise to a solution of 12.1 g dry DIPA (120 mmol) in 250 mL dry THF at −78° C. under argon atmosphere. The mixture was stirred for 30 minutes at the same temperature then 28.0 g (4-bromo-2-chloro-phenoxy)-trimethyl-silane (100 mmol) was added dropwise. After 2.5 hours 21.3 g MeI (150 mmol) was added dropwise then the cooling bath was removed and the mixture was stirred overnight. The reaction was quenched with 100 mL NH$_4$OH solution and 200 mL NH$_4$Cl solution and extracted with EtOAc, dried over Na$_2$SO$_4$, filtered and concentrated under reduced pressure. The resulting dark mass was refluxed with pure hexane several times (150-150 mL aliquots) and decanted leaving a black tar behind. Combined organic phases were concentrated under reduced pressure affording 19.0 g crude product used without further purification. $^1$H NMR (200 MHz, CDCl$_3$): 7.32 (d, 1H), 6.76 (d, 1H), 5.62 (s, 1H), 2.49 (s, 3H)

Step C: (4-Bromo-2-chloro-3-methyl-phenoxy)-trimethyl-silane 20.8 g HMDS (129 mmol) was added to the solution of 19.0 g 4-bromo-2-chloro-3-methyl-phenol (86.0 mmol) in 150 mL dry THF. The mixture was stirred at 85° C. under argon balloon for 1.5 hours and then concentrated under reduced pressure. The obtained product was used without further purification. $^1$H NMR (200 MHz, CDCl$_3$): 7.30 (d, 1H), 6.63 (d, 1H), 2.50 (s, 3H), 0.28 (s, 9H)

Step D: Preparation 6

A solution of 25.2 g (4-bromo-2-chloro-3-methyl-phenoxy)-trimethyl-silane (86.0 mmol) in 250 mL dry THF was cooled to −78° C. under argon and then 38 mL nBuLi in hexanes (2.5 M, 94.6 mmol) was added dropwise. After 5 minutes 19.2 g 2-isopropoxy-4,4,5,5-tetramethyl-1,3,2-dioxaborolane (103 mmol) was added dropwise. The cooling bath was removed and the mixture was slowly allowed to warm up to r.t. Then the mixture was added to 200 mL NH$_4$Cl solution and extracted with EtOAc. Combined organic layers were concentrated under reduced pressure and passed through a pad of silica gel using hexane and EtOAc as eluents. The crude product was recrystallized from a mixture of EtOAc and hexane to obtain Preparation 6. $^1$H NMR (500 MHz, DMSO-$d_6$): 10.40 (s, 1H), 7.42 (d, 1H), 6.80 (d, 1H), 2.49 (s, 3H), 1.27 (s, 12H)

Preparation 7: Ethyl (2R)-2-[(5S$_a$)-5-(3-chloro-4-hydroxy-2-methyl-phenyl)-6-(4-fluorophenyl)thieno[2,3-d]pyrimidin-4-yl]oxy-3-(2-tetrahydropyran-2-yloxyphenyl) propanoate 186.6 g Preparation 5 (310.3 mmol) and 99.99 g Preparation 6 (372.3 mmol) were dissolved in 1.2 L THF, then 202.2 g Cs$_2$CO$_3$ (620.6 mmol) dissolved in 300 mL water was added. Then 11.0 g AtaPhos (15.51 mmol) was added, and the mixture was stirred under nitrogen at reflux temperature until no further conversion was observed. Most of the volatiles were evaporated under reduced pressure, then it was diluted with DCM and brine. After shaking the pH of the aqueous phase was set to 8 with 2M HCl. After phase separation the aqueous phase was extracted with DCM. The organic layers were combined and dried over Na$_2$SO$_4$, filtered and concentrated under reduced pressure. The diastereoisomers were separated via flash chromatography using heptane and ethyl acetate as eluents. The diastereoisomer pair eluting later was collected as Preparation 7.

$^1$H NMR (500 MHz, DMSO-$d_6$, 1:1 mixture of diastereomers): 10.27 (br s, 1H), 8.60 (s, 1H), 7.30 (m, 2H), 7.22 (m, 2H), 7.16-7.14 (d, 1H), 7.12 (m, 1H), 7.00 (d, 1H), 6.96 (d, 1H), 6.74-6.73 (t, 1H), 6.34-6.36 (d, 1H), 5.55-5.52 (m, 1H), 5.54-5.41 (dd, 1H), 4.06 (q, 2H), 3.68-3.54 (m, 2H), 3.10-3.07 (dd, 1H), 2.44 (dd, 1H), 1.98-1.90 (br s, 1H), 1.85-1.83 (s, 3H), 1.79 (br s, 2H), 1.64 (br s, 1H), 1.59 (br s, 1H), 1.54 (br s, 1H), 1.09-1.08 (t, 3H) HRMS: (M+H)=663.1728 and 663.1717

Preparation 8: Ethyl (2R)-2-[(5S$_a$)-5-[3-chloro-2-methyl-4-[2-(4-methylpiperazin-1-yl)ethoxy]phenyl]-6-(4-fluorophenyl)thieno[2,3-d]pyrimidin-4-yl] oxy-3-(2-tetrahydro pyran-2-yloxyphenyl) propanoate 132.3 g Preparation 7 (199.5 mmol), 43.17 g 2-(4-methylpiperazin-1-yl)ethanol (299.3 mmol) and 94.20 g PPh$_3$ (359.1 mmol) were dissolved in 1 L dry toluene, then 78.09 g di-tert-butyl azodicarboxylate (339.2 mmol) was added. The mixture was stirred at 50° C. under N$_2$ until no further conversion was observed. 980 mL toluene was evaporated, then 500 mL Et$_2$O was added, and the mixture was stirred and sonicated. The precipitated white crystals were filtered, washed with Et$_2$O to give 65.9 g pure triphenylphosphineoxide. The filtrate was concentrated under reduced pressure and purified via flash chromatography using EtOAc and MeOH as eluents to obtain Preparation 8. MS: (M+H)$^+$=789.2

Preparation 9: Ethyl (2R)-2-[(5S$_a$)-[3-chloro-2-methyl-4-[2-(4-methylpiperazin-1-yl) ethoxy]phenyl]-6-(4-fluorophenyl)thieno[2,3-d]pyrimidin-4-yl] oxy-3-(2-hydroxy phenyl)propanoate 199.5 mmol Preparation 8 was dissolved in 1 L EtOH, then 1 L 1.25M HCl in EtOH was added and the mixture was stirred at r.t. until no further conversion was observed. Most of the EtOH was evaporated, then Et$_2$O was added and the precipitated HCl salt (white solid) was filtered, washed with Et$_2$O. The HCl salt was carefully treated with saturated NaHCO$_3$ solution, extracted with DCM, the combined organic phases were dried over Na$_2$SO$_4$, filtered and concentrated under reduced pressure to give Preparation 9.

$^1$H NMR (400 MHz, DMSO-d$_6$): 9.53 (br s, 1H), 8.60 (s, 1H), 7.30 (m, 2H), 7.28 (d, 1H), 7.21 (m, 2H), 7.16 (d, 1H), 6.97 (t, 1H), 6.72 (d, 1H), 6.53 (t, 1H), 6.20 (d, 1H), 5.46 (dd, 1H), 4.22 (m, 2H), 4.04 (m, 2H), 2.92 (dd, 1H), 2.75 (m, 2H), 2.53 (br s, 4H), 2.44 (dd, 1H), 2.36 (br s, 4H), 2.17 (s, 3H), 1.88 (s, 3H), 1.06 (t, 3H)

HRMS calculated for C$_{37}$H$_{38}$ClFN$_4$O$_5$S: 704.2235, found: 705.2288 (M+H)

Preparation 10: (E)-4-(Dimethylamino)-1,1-dimethoxy—but-3-en-2-one 502.1 g 1,1-dimethoxypropan-2-one (4.25 mol) and 506.4 g 1,1-dimethoxy-N,N-dimethyl-methanamine (4.25 mol) were mixed in a 2 L flask and stirred at 105° C. for 3 hours. The formed MeOH was removed continuously via distillation. When MeOH formation stopped (at 65° C. head temperature) the reaction mixture was vacuum distilled (decreasing the pressure slowly to 30 mbar) to remove side products and unreacted starting materials. The crude product was distilled at 0.1 mbar. Fractions were collected between 107-118° C. head temperature (bath temperature 160-165° C.) to give a yellow oil. $^1$H NMR (500 MHz, DMSO-d$_6$): 7.59 (d, 1H), 5.17 (d, 1H), 4.42 (s, 1H), 3.25 (s, 6H), 3.09 (s, 3H), 2.78 (s, 3H)

Preparation 11: [2-(2-Methoxyphenyl)pyrimidin-4-yl]methanol

Step A: 4-(dimethoxymethyl)-2-(2-methoxyphenyl)pyrimidine

To the mixture of 2-methoxybenzamidine hydrochloride (1.2 eq.) and Preparation 10 (1 eq.) in dry methanol (0.5 mL/mmol) sodium methoxide (1.2 eq.) was added portionwise and the mixture was stirred at 75° C. for 2 hours. The reaction mixture was cooled and concentrated under reduced pressure. To the residue water was added and it was extracted with DCM. The combined organic layers were dried over MgSO$_4$, filtered and concentrated under reduced pressure. The crude product was purified via flash chromatography using heptane and EtOAc as eluents. $^1$H NMR (400 MHz, DMSO-d$_6$): 8.93 (d, 1H), 7.55-7.44 (m, 3H), 7.16 (d, 1H), 7.06 (m, 1H), 5.31 (s, 1H), 3.76 (s, 3H), 3.37 (s, 6H)

Step B: Preparation 11

261 mg 4-(dimethoxymethyl)-2-(2-methoxyphenyl)pyrimidine (1.0 mmol) was dissolved in 2 mL HCl in dioxane (4M solution), then 2 mL water was added and this mixture was stirred at 50° C. for 16 hours. The reaction mixture was cooled to 0° C., then 320 mg NaOH (8.0 mmol) was added portionwise. The pH was adjusted to 8 using 10% K$_2$CO$_3$ solution, then 76 mg sodium borohydride (2.0 mmol) was added and the mixture was stirred for 30 minutes at 0° C. The reaction mixture was diluted with 5 mL water and extracted with EtOAc. The combined organic phases were dried over Na$_2$SO$_4$ and concentrated under reduced pressure. The crude product was purified via flash chromatography using heptane and EtOAc as eluents to give Preparation 11.

$^1$H NMR (400 MHz, DMSO-d$_6$): 8.84 (d, 1H), 7.50-7.42 (m, 3H), 7.14 (d, 1H), 7.03 (m, 1H), 5.66 (t, 1H), 4.58 (d, 2H), 3.75 (s, 3H)

Preparation 12: (2R)-2-{[(5S$_a$)-5-{3-chloro-2-methyl-4-[2-(4-methylpiperazin-1-yl) ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic Acid Step A 1 eq. Preparation 9, 2 eq. of Preparation 11 and 2 eq. triphenyl phosphine were dissolved in absolute toluene (0.2M for the phenol), then 2 eq. di-tert-butyl azodicarboxylate was added. The mixture was stirred at 50° C. under nitrogen until no further conversion was observed. The volatiles were evaporated under reduced pressure and the crude intermediate was purified via flash chromatography using ethyl acetate and methanol as eluents.

Step B

The obtained intermediate was dissolved in dioxane-water 1:1 (10 mL/mmol) and 10 eq. LiOH×H$_2$O was added. The mixture was stirred at r.t. until no further conversion was observed. Then it was diluted with brine, neutralized with 2M HCl, extracted with DCM. The combined organic phases were dried over Na$_2$SO$_4$, filtered and concentrated under reduced pressure and purified via preparative reversed phase chromatography using 25 mM aqueous NH$_4$HCO$_3$ solution and MeCN as eluents. HRMS calculated for C$_{47}$H$_{44}$ClFN$_6$O$_6$S: 874.2716; found 438.1415 (M+2H)

Preparation 13: (2R)-2-{[5-{3,5-dichloro-2,6-dimethyl-4-[2-(4-methylpiperazin-1-yl) ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic Acid Step A: 4-bromo-2,6-dichloro-3,5-dimethyl-phenol 30.16 g 4-bromo-3,5-dimethyl-phenol (150 mmol) was dissolved in a mixture of 75 mL 1,2-dichloroethane and 75 mL acetonitrile, then 40.06 g NCS (300 mmol) was added portionwise and the mixture was stirred at r.t. until no further conversion was observed. Reaction mixture was concentrated under reduced pressure, the residue was dissolved in DCM, washed with water and brine. The organic layer was dried over Na$_2$SO$_4$ and concentrated under reduced pressure and used in the next step without further purification. NMR (400 MHz, DMSO-d$_6$): 10.10 (s, 1H), 2.46 (s, 6H)

Step B: 1-bromo-3,5-dichloro-4-methoxy-2,6-dimethyl-benzene

To a solution of 26.0 g 4-bromo-2,6-dichloro-3,5-dimethyl-phenol (96.3 mmol) and 26.60 g K$_2$CO$_3$ (192.6 mmol) in 300 mL MeCN 6.6 mL MeI (105.9 mmol) was added and the mixture was stirred at r.t. until no further conversion was observed. The solids were filtered off and the filtrate was concentrated under reduced pressure. The crude product was dissolved in DCM, washed with water and brine. The organic layer was dried over Na$_2$SO$_4$ and concentrated under reduced pressure and used in the next step without further purification. $^1$H NMR (400 MHz, DMSO-d$_6$): 3.78 (s, 3H), 2.49 (s, 6H)

Step C: 2-(3,5-dichloro-4-methoxy-2,6-dimethylphenyl)-4,4,5,5-tetramethyl-1,3,2-dioxaborolane 10.0 g 1-bromo-3,5-dichloro-4-methoxy-2,6-dimethyl-benzene (35.2 mmol) was dissolved in 360 mL dry THF under nitrogen and was cooled to −78° C. with dry ice-acetone. 23.2 mL nBuLi (1.6 M in hexanes) (37.0 mmol) was added and the mixture was stirred for 15 minutes, then 8.6 mL 2-isopropoxy-4,4,5,5-tetramethyl-1,3,2-dioxaborolane (42.24 mmol) was added and the mixture was allowed to warm up to r.t. It was quenched with brine, extracted with DCM, dried over $Na_2SO_4$, filtered and concentrated under reduced pressure. The crude product was purified via flash chromatography using heptane and EtOAc as eluents to obtain 2-(3,5-dichloro-4-methoxy-2,6-dimethyl-phenyl)-4,4,5,5-tetramethyl-1,3,2-dioxaborolane. $^1$H NMR (400 MHz, DMSO-$d_6$): 3.81 (s, 3H), 2.33 (s, 6H), 1.34 (s, 12H)

Step D: ethyl 4-(3,5-dichloro-4-methoxy-2,6-dimethyl-phenyl)thiophene-3-carboxylate 3.92 g ethyl 4-bromothiophene-3-carboxylate (16.68 mmol) and 9.9 g 2-(3,5-dichloro-4-methoxy-2,6-dimethyl-phenyl)-4,4,5,5-tetramethyl-1,3,2-dioxaborolane (30.0 mmol) were dissolved in 140 mL dioxane, then 10.87 g $CS_2CO_3$ (33.36 mmol) dissolved in 40 mL water was added. Then 590 mg AtaPhos (0.83 mmol) was added, and the mixture was stirred under nitrogen at reflux temperature until no further conversion was observed. Then it was diluted with DCM and brine. After phase separation the aqueous phase was extracted with DCM. The organic layers were combined and dried over $Na_2SO_4$, filtered and concentrated under reduced pressure. The crude product was purified via flash chromatography using heptane and EtOAc as eluents to obtain ethyl 4-(3,5-dichloro-4-methoxy-2,6-dimethyl-phenyl)thiophene-3-carboxylate.
$^1$H NMR (400 MHz, DMSO-$d_6$): 8.53 (d, 1H), 7.47 (d, 1H), 4.02 (q, 2H), 3.83 (s, 3H), 1.95 (s, 6H), 1.00 (t, 3H)
HRMS (M+NH$_4$)$^+$=376.0538

Step E: ethyl 4-(3,5-dichloro-4-methoxy-2,6-dimethyl-phenyl)-2,5-diiodo-thiophene-3-carboxylate 2.65 g 4-(3,5-dichloro-4-methoxy-2,6-dimethyl-phenyl) thiophene-3-carboxylate (7.38 mmol) was dissolved in 75 mL acetonitrile, then 2.2 mL fluoroboric acid diethyl ether complex (16.23 mmol) and 3.65 g N-iodosuccinimide (16.23 mmol) was added and the mixture was stirred at r.t. until no further conversion was observed. Reaction mixture was concentrated under reduced pressure, and the crude product was purified via flash chromatography using heptane and EtOAc as eluents to obtain ethyl 4-(3,5-dichloro-4-methoxy-2,6-dimethyl-phenyl)-2,5-diiodo-thiophene-3-carboxylate. $^1$H NMR (400 MHz, DMSO-$d_6$): 3.98 (q, 2H), 3.84 (s, 3H), 1.92 (s, 6H), 0.84 (t, 3H)

Step F: ethyl 4-(3,5-dichloro-4-methoxy-2,6-dimethyl-phenyl)-5-iodo-thiophene-3-carboxylate 5.29 g 4-(3,5-dichloro-4-methoxy-2,6-dimethyl-phenyl)-2,5-diiodo-thiophene-3-carboxylate (8.66 mmol) was dissolved in 90 mL dry THF, then cooled to −78° C. under argon atmosphere. 6.7 mL isopropyl magnesium chloride, lithium chloride complex (1.3 M in THF) (8.66 mmol) was added and the mixture was stirred at −78° C. for 30 minutes. Then saturated aqueous NH$_4$Cl was added and the mixture was extracted with ethyl acetate. The organic layer was dried over $Na_2SO_4$ and concentrated under reduced pressure. The crude product was purified via flash chromatography using heptane and EtOAc as eluents to obtain ethyl 4-(3,5-dichloro-4-methoxy-2,6-dimethyl-phenyl)-5-iodo-thiophene-3-carboxylate. $^1$H NMR (400 MHz, DMSO-$d_6$): 8.71 (s, 1H), 4.01 (q, 2H), 3.86 (s, 3H), 1.89 (s, 6H), 0.99 (t, 3H)

Step G: ethyl 4-(3,5-dichloro-4-methoxy-2,6-dimethyl-phenyl)-5-(4-fluorophenyl)thiophene-3-carboxylate 4.20 g ethyl 4-(3,5-dichloro-4-methoxy-2,6-dimethyl-phenyl)-5-iodo-thiophene-3-carboxylate (8.66 mmol) and 1.82 g 4-fluorophenylboronic acid (13.0 mmol) were dissolved in 80 mL dioxane, then 5.64 g $CS_2CO_3$ (17.32 mmol) dissolved in 20 mL water was added. Then 500 mg Pd(PPh$_3$)$_4$ (0.43 mmol) was added, and the mixture was stirred under nitrogen at 80° C. until no further conversion was observed. Then it was diluted with DCM and brine. After phase separation the aqueous phase was extracted with DCM. The organic layers were combined and dried over $Na_2SO_4$, filtered and concentrated under reduced pressure. The crude product was purified via flash chromatography using heptane and EtOAc as eluents to obtain ethyl 4-(3,5-dichloro-4-methoxy-2,6-dimethyl-phenyl)-5-(4-fluorophenyl)thiophene-3-carboxylate.
$^1$H NMR (400 MHz, DMSO-$d_6$): 8.58 (s, 1H), 7.22-7.10 (m, 4H), 4.03 (q, 2H), 3.82 (s, 3H), 1.92 (s, 6H), 1.00 (t, 3H)
HRMS (M+H)$^+$=453.0498

Step H: ethyl 4-(3,5-dichloro-4-methoxy-2,6-dimethyl-phenyl)-5-(4-fluorophenyl)-2-nitro-thiophene-3-carboxylate 1.97 g ethyl 4-(3,5-dichloro-4-methoxy-2,6-dimethyl-phenyl)-5-(4-fluorophenyl)thiophene-3-carboxylate (4.34 mmol) was dissolved in 40 mL dry acetonitrile, then 576 mg nitronium tetrafluoroborate (4.34 mmol) was added and the mixture was stirred at r.t. until no further conversion was observed. Then it was diluted with DCM and brine. After phase separation the aqueous phase was extracted with DCM. The organic layers were combined and dried over $Na_2SO_4$, filtered and concentrated under reduced pressure. The crude product was purified via flash chromatography using heptane and EtOAc as eluents to obtain ethyl 4-(3,5-dichloro-4-methoxy-2,6-dimethyl-phenyl)-5-(4-fluorophenyl)-2-nitro-thiophene-3-carboxylate. $^1$H NMR (400 MHz, DMSO-$d_6$): 7.37-7.33 (m, 2H), 7.32-7.26 (m, 2H), 4.14 (q, 2H), 3.82 (s, 3H), 2.06 (s, 6H), 0.88 (t, 3H)

Step I: ethyl 2-amino-4-(3,5-dichloro-4-methoxy-2, 6-dimethyl-phenyl)-5-(4-fluorophenyl)thiophene-3-carboxylate 1.85 g ethyl 4-(3,5-dichloro-4-methoxy-2,6-dimethyl-phenyl)-5-(4-fluorophenyl)-2-nitro-thiophene-3-carboxylate (3.71 mmol) was dissolved in a mixture of 90 mL acetic acid and 18 mL water, then 2.43 g zinc dust (37.1 mmol) was added portionwise and the mixture was stirred at r.t. until no further conversion was observed. Reaction mixture was concentrated under reduced pressure, and the crude product was purified via flash chromatography using heptane and EtOAc as eluents to obtain ethyl 2-amino-4-(3,5-dichloro-4-methoxy-2,6-dimethyl-phenyl)-5-(4-fluorophenyl)thiophene-3-carboxylate.
$^1$H NMR (400 MHz, DMSO-$d_6$): 7.73 (s, 2H), 7.12-7.06 (m, 2H), 7.02-6.97 (m, 2H), 3.86-3.80 (m, 2H), 3.80 (s, 3H), 2.01 (s, 6H), 0.72 (t, 3H)
HRMS (M+H)$^+$=456.0598

Step J: 5-(3,5-dichloro-4-methoxy-2,6-dimethyl-phenyl)-6-(4-fluorophenyl)-3H-thieno[2,3-d]pyrimidin-4-one 1.10 g ethyl 2-amino-4-(3,5-dichloro-4-methoxy-2,6-dimethyl-phenyl)-5-(4-fluorophenyl)thiophene-3-carboxylate (2.35 mmol) was dissolved in 20 mL formamide and it was stirred at 150° C. until no further conversion was observed. Then it was poured onto water and the precipitated product was collected by filtration to give 5-(3,5-dichloro-4-methoxy-2,6-dimethyl-phenyl)-6-(4-fluorophenyl)-3H-thieno[2,3-d]pyrimidin-4-one.

$^1$H NMR (400 MHz, DMSO-$d_6$): 12.53 (br s, 1H), 8.18 (s, 1H), 7.23-7.16 (m, 4H), 3.84 (s, 3H), 1.96 (s, 6H)

HRMS (M+H)$^+$=449.0289

Step K: 4-chloro-5-(3,5-dichloro-4-methoxy-2,6-dimethyl-phenyl)-6-(4-fluorophenyl)thieno[2,3-d]pyrimidine 700 mg 5-(3,5-dichloro-4-methoxy-2,6-dimethyl-phenyl)-6-(4-fluorophenyl)-3H-thieno[2,3-d]pyrimidin-4-one (1.56 mmol) was dissolved in 6 mL phosphorous oxychloride and it was stirred at 90° C. until no further conversion was observed. Reaction mixture was concentrated under reduced pressure, then to the crude product icy water was added and it was sonicated for 10 minutes. The precipitated product was collected by filtration to give 4-chloro-5-(3,5-dichloro-4-methoxy-2,6-dimethyl-phenyl)-6-(4-fluorophenyl)thieno[2,3-d]pyrimidine.

$^1$H NMR (400 MHz, DMSO-$d_6$): 9.02 (s, 1H), 7.38-7.26 (m, 4H), 3.86 (s, 3H), 1.99 (s, 6H) HRMS (M+H)$^+$=466.9954

Step L: 2,6-dichloro-4-[4-chloro-6-(4-fluorophenyl)thieno[2,3-d]pyrimidin-5-yl]-3,5-dimethyl-phenol and 4-[4-bromo-6-(4-fluorophenyl)thieno[2,3-d]pyrimidin-5-yl]-2,6-dichloro-3,5-dimethyl-phenol To a stirred solution of 700 mg 4-chloro-5-(3,5-dichloro-4-methoxy-2,6-dimethyl-phenyl)-6-(4-fluorophenyl)thieno[2,3-d]pyrimidine (1.50 mmol) in 15 mL DCM 3.0 mL boron tribromide (1 M in DCM) (3.0 mmol) was added at 0° C. and the mixture was allowed to warm up to r.t. and it was stirred until no further conversion was observed. The mixture was quenched with saturated aqueous NH$_4$Cl and extracted with DCM. The combined organic phases were dried over Na$_2$SO$_4$ and concentrated under reduced pressure. The residue was purified via flash chromatography using heptane and EtOAc as eluents to obtain 2,6-dichloro-4-[4-chloro-6-(4-fluorophenyl)thieno[2,3-d]pyrimidin-5-yl]-3,5-dimethyl-phenol and 4-[4-bromo-6-(4-fluorophenyl)thieno[2,3-d]pyrimidin-5-yl]-2,6-dichloro-3,5-dimethyl-phenol as a 37:63 mixture of products.

$^1$H NMR (400 MHz, DMSO-$d_6$): 10.14 (br s, 1H), 9.01 (s, 1H), 7.40-7.23 (m, 4H), 1.95 (s, 6H) and 10.14 (br s, 1H), 8.93 (s, 1H), 7.40-7.23 (m, 4H), 1.93 (s, 6H)

HRMS (M+H)$^+$=452.9800 and 496.9287

Step M: 4-chloro-5-[3,5-dichloro-2,6-dimethyl-4-[2-(4-methylpiperazin-1-yl)ethoxy]phenyl]-6-(4-fluorophenyl)thieno[2,3-d]pyrimidine and 4-bromo-5-[3,5-dichloro-2,6-dimethyl-4-[2-(4-methylpiperazin-1-yl)ethoxy]phenyl]-6-(4-fluorophenyl)thieno[2,3-d]pyrimidine 300 mg mixture of 2,6-dichloro-4-[4-chloro-6-(4-fluorophenyl)thieno[2,3-d]pyrimidin-5-yl]-3,5-dimethyl-phenol and 4-[4-bromo-6-(4-fluorophenyl)thieno[2,3-d]pyrimidin-5-yl]-2,6-dichloro-3,5-dimethyl-phenol (0.62 mmol), 286 mg 2-(4-methylpiperazin-1-yl)ethanol (1.98 mmol) and 520 mg triphenyl phosphine (1.98 mmol) were dissolved in 10 mL dry toluene, then 460 mg ditert-butyl azodicarboxylate (1.98 mmol) was added. The mixture was stirred at 50° C. under nitrogen until no further conversion was observed. The volatiles were evaporated under reduced pressure and the crude intermediate was purified via flash chromatography using EtOAc and methanol as eluents to obtain 4-chloro-5-[3,5-dichloro-2,6-dimethyl-4-[2-(4-methylpiperazin-1-yl)ethoxy]phenyl]-6-(4-fluorophenyl)thieno[2,3-d]pyrimidine and 4-bromo-5-[3,5-dichloro-2,6-dimethyl-4-[2-(4-methylpiperazin-1-yl)ethoxy]phenyl]-6-(4-fluorophenyl)thieno[2,3-d]pyrimidine as a 35:65 mixture of products.

$^1$H NMR (400 MHz, DMSO-$d_6$): 9.02 (S, 1H), 7.40-7.22 (m, 4H), 4.11 (t, 2H), 2.78 (t, 2H), 2.63-2.20 (m, 8H), 2.17 (br s, 3H), 1.98 (s, 6H) and 8.94 (S, 1H), 7.40-7.22 (m, 4H), 4.11 (t, 2H), 2.78 (t, 2H), 2.63-2.20 (m, 8H), 2.15 (br s, 3H), 1.98 (s, 6H)

HRMS (M+H)$^+$=579.0968 and 623.0455

Step N: (E)-4-(Dimethylamino)-1,1-dimethoxy-but-3-en-2-one 502.1 g 1,1-dimethoxypropan-2-one (4.25 mol) and 506.4 g 1,1-dimethoxy-N,N-dimethyl-methanamine (4.25 mol) were mixed in a 2 L flask and stirred at 105° C. for 3 hours. The formed MeOH was removed continuously via distillation. When MeOH formation stopped (at 65° C. head temperature), the reaction mixture was vacuum distilled (decreasing the pressure slowly to 30 mbar) to remove side products and unreacted starting materials. The crude product was distilled at 0.1 mbar. Fractions were collected between 107-118° C. head temperature (bath temperature 160-165° C.) to give a yellow oil. $^1$H NMR (500 MHz, DMSO-$d_6$): 7.59 (d, 1H), 5.17 (d, 1H), 4.42 (s, 1H), 3.25 (s, 6H), 3.09 (s, 3H), 2.78 (s, 3H)

Step O: 4-(dimethoxymethyl)-2-(2-methoxyphenyl)pyrimidine

To the mixture of 2-methoxybenzamidine acetic acid salt (1.2 eq.) and (E)-4-(dimethylamino)-1,1-dimethoxy-but-3-en-2-one (1.0 eq.) in dry methanol (0.5 mL/mmol) sodium methoxide (1.2 eq.) was added portionwise and the mixture was stirred at 75° C. for 2 hours. The reaction mixture was cooled and concentrated under reduced pressure. To the residue water was added and it was extracted with DCM. The combined organic layers were dried over MgSO$_4$, filtered and concentrated under reduced pressure. The crude product was purified via flash chromatography using heptane and EtOAc as eluents to give 4-(dimethoxymethyl)-2-(2-methoxyphenyl)pyrimidine. $^1$H NMR (400 MHz, DMSO-$d_6$): 8.93 (d, 1H), 7.55-7.44 (m, 3H), 7.16 (d, 1H), 7.06 (m, 1H), 5.31 (s, 1H), 3.76 (s, 3H), 3.37 (s, 6H)

Step P: [2-(2-methoxyphenyl)pyrimidin-4-yl]methanol 261 mg 4-(dimethoxymethyl)-2-(2-methoxyphenyl)pyrimidine (1.00 mmol) was dissolved in 2 mL HCl in dioxane (4 M solution), then 2 mL water was added and this mixture was stirred at 50° C. for 16 hours. The reaction mixture was cooled to 0° C., then 320 mg NaOH (8.0 mmol) was added portionwise. The pH was adjusted to 8 using 10% K$_2$CO$_3$ solution, then 76 mg sodium borohydride (2.0 mmol) was added and the mixture was stirred for 30 minutes at 0° C. The reaction mixture was diluted with 5 mL water and extracted with EtOAc. The combined organic phases were dried over $Na_2SO_4$ and concentrated under reduced pressure. The crude product was purified via flash chromatography using heptane and EtOAc as eluents to give the title product. $^1H$ NMR (400 MHz, DMSO-$d_6$): 8.84 (d, 1H), 7.50-7.42 (m, 3H), 7.14 (d, 1H), 7.03 (m, 1H), 5.66 (t, 1H), 4.58 (d, 2H), 3.75 (s, 3H)

Step Q: (2R)-2-Hydroxy-3-[2-[[2-(2-methoxyphenyl)pyrimidin-4-yl]methoxy]phenyl]propanoic Acid 37.84 g (150 mmol) Preparation 3, 48.65 g (225 mmol) [2-(2-methoxyphenyl)pyrimidin-4-yl]methanol and 59.01 g (225 mmol) triphenyl phosphine were dissolved in 160 mL absolute toluene, then 102.47 mL (225 mmol) diethylazodicarboxylate was added. The mixture was stirred at 50° C. under nitrogen until no further conversion was observed. The volatiles were evaporated under reduced pressure. Then 400 mL $Et_2O$ was added, the mixture was sonicated and filtered (to remove $PPh_3$). $Et_2O$ was removed in vacuo. Residue was dissolved in 130 mL THF, then 30 g NaOH in 130 mL $H_2O$ was added. The mixture was stirred at r.t. until no further conversion was observed. Then it was acidified with 2 M HCl, THF was removed in vacuo. 300 mL DCM was added, and the precipitate was filtered, washed with cold $H_2O$ and DCM dried in vacuo to obtain(2R)-2-hydroxy-3-[2-[[2-(2-methoxyphenyl)pyrimidin-4-yl]methoxy]phenyl]propanoic acid. $^1H$-NMR (400 MHz, DMSO-$d_6$): 8.88 (d, 1H), 7.80 (d, 1H), 7.55 (dd, 1H), 7.49-7.44 (m, 1H), 7.26 (dd, 1H), 7.17-7.11 (m, 2H), 7.06 (t, 1H), 6.98 (d, 1H), 6.88 (t, 1H), 5.22 (s, 2H), 3.81 (dd, 1H), 3.77 (s, 3H), 3.73 (dd, 1H), 2.44 (dd, 1H)

Step R: Ethyl (2R)-2-hydroxy-3-[2-[[2-(2-methoxyphenyl)pyrimidin-4-yl]methoxy]phenyl]propanoate 51.7 g (136 mmol) (2R)-2-hydroxy-3-[2-[[2-(2-methoxyphenyl)pyrimidin-4-yl]methoxy]phenyl]propanoic acid was dissolved in 520 mL EtOH, then 20 mL concentrated $H_2SO_4$ was added. The mixture was stirred at 60° C. until no further conversion was observed. Then it was diluted with water, neutralized with concentrated $NaHCO_3$ solution and extracted with DCM. The combined organic phases were dried over $Na_2SO_4$, filtered and concentrated under reduced pressure and purified via flash chromatography using EtOAc and MeOH as eluents to obtain ethyl (2R)-2-hydroxy-3-[2-[[2-(2-methoxyphenyl)pyrimidin-4-yl]methoxy]phenyl]propanoate. HRMS calculated for $C_{23}H_{24}N_2O_5$: 408.1685, found: 409.1757 (M+H)

Step S: Preparation 13

200 mg mixture of 4-chloro-5-[3,5-dichloro-2,6-dimethyl-4-[2-(4-methylpiperazin-1-yl) ethoxy]phenyl]-6-(4-fluorophenyl)thieno[2,3-d]pyrimidine and 4-bromo-5-[3,5-dichloro-2,6-dimethyl-4-[2-(4-methylpiperazin-1-yl) ethoxy]phenyl]-6-(4-fluorophenyl)thieno[2,3-d]pyrimidine (0.33 mmol), 211 mg ethyl (2R)-2-hydroxy-3-[2-[[2-(2-methoxyphenyl)pyrimidin-4-yl]methoxy]phenyl]propanoate (0.52 mmol) and 202 mg $Cs_2CO_3$ (0.62 mmol) was dissolved in 5 mL tert-butanol and the mixture was stirred at 70° C. until no further conversion was observed. It was diluted with ethyl acetate and then it was washed with brine. The organic layer was dried over $Na_2SO_4$, filtered and concentrated under reduced pressure and purified via flash chromatography using EtOAc and methanol as eluents to obtain ethyl (2R)-2-[5-[3,5-dichloro-2,6-dimethyl-4-[2-(4-methylpiperazin-1-yl)ethoxy]phenyl]-6-(4-fluorophenyl) thieno[2,3-d]pyrimidin-4-yl]oxy-3-[2-[[2-(2-methoxyphenyl)pyrimidin-4-yl]methoxy]phenyl]propanoate.

The obtained intermediate was dissolved in 5 mL dioxane-water 1:1 (10 mL/mmol) and 145 mg LiOH×$H_2O$ (3.45 mmol) was added. The mixture was stirred at r.t. until no further conversion was observed. Then it was diluted with brine, neutralized with 2 M HCl, extracted with DCM, dried over $Na_2SO_4$, filtered and concentrated under reduced pressure and purified via preparative reversed phase chromatography using 5 mM aqueous $NH_4HCO_3$ solution and MeCN as eluents to obtain Preparation 13.

$^1H$ NMR (400 MHz, DMSO-$d_6$): 8.89 (d, 1H), 8.60 (s, 1H), 7.81 (d, 1H), 7.53 (dd, 1H), 7.45 (td, 1H), 7.29-7.21 (m, 4H), 7.17-7.13 (m, 1H), 7.14 (d, 1H), 7.04 (td, 1H), 7.01 (d, 1H), 6.76 (t, 1H), 6.20 (d, 1H), 5.45 (dd, 1H), 5.26 (d, 1H), 5.20 (d, 1H), 4.06-4.01 (m, 2H), 3.76 (s, 3H), 3.46 (dd, 1H), 2.79-2.74 (m, 2H), 2.67-2.38 (m, 8H), 2.33 (s, 3H), 2.26 (s, 3H), 2.22 (dd, 1H), 1.73 (s, 3H) HRMS $(M+2H)^{2+}$ =462.1310

Preparation 14: (2R)-2-{[5-{2,6-dimethyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxy phenyl)pyrimidin-4-yl]methoxy}phenyl) propanoic Acid Using the procedure as described in Preparation 13 and starting directly from Step B with 4-bromo-3,5-dimethylphenol instead of 4-bromo-2,6-dichloro-3,5-dimethyl-phenol, Preparation 14 is obtained.

Example 1: 1-[(methoxycarbonyl)oxy]ethyl (2R)-2-{[(5S$_a$)-5-{3-chloro-2-methyl-4-[2-(4-methylpiperazin-1-yl)ethoxy]phenyl}-6-(4-fluorophenyl)thieno [2,3-d]pyrimidin-4-yl]oxy}-3-{[2-(2-methoxyphenyl)pyrimidin-4-yl]methoxy}phenyl) propanoate Using General procedure I with Preparation 12 and methanol as the appropriate alcohol, Example 1 was obtained. HRMS calculated for $C_{51}H_{50}ClFN_6O_9S$: 976.3033; found 489.1604 and 489.1572 (M+2H)

Example 2: 1-[(ethoxycarbonyl)oxy]ethyl (2R)-2-{ [(5S$_a$)-5-{3-chloro-2-methyl-4-[2-(4-methylpiperazin-1-yl)ethoxy]phenyl}-6-(4-fluorophenyl)thieno [2,3-d]pyrimidin-4-yl]oxy}-3-(2-{[2-(2-methoxyphenyl)pyrimidin-4-yl]methoxy}phenyl) propanoate Using General procedure I with Preparation 12 and ethanol as the appropriate alcohol, Example 2 was obtained. HRMS calculated for $C_{52}H_{52}ClFN_6O_9S$: 990.3189; found 496.1649 and 496.1685 (M+2H).

Example 3: 1-{[(propan-2-yloxy)carbonyl]oxy}ethyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate Using General procedure I with Preparation 12 and 2-propanol as the appropriate alcohol, Example 3 was obtained. HRMS calculated for $C_{53}H_{54}ClFN_6O_9S$: 1004.3345; found 503.1766 (M+2H)

Example 4: 1-[(tert-butoxycarbonyl)oxy]ethyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate Using General procedure I with Preparation 12 and 2-methyl-2-propanol as the appropriate alcohol, Example 4 was obtained. HRMS calculated for $C_{54}H_{56}ClFN_6O_9S$: 1018.3502; found 510.1837 (M+2H)

Example 5: 1-{[(cyclopentyloxy)carbonyl]oxy}ethyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate Using General procedure I with Preparation 12 and cyclopentanol as the appropriate alcohol, Example 5 was obtained. HRMS calculated for $C_{55}H_{56}ClFN_6O_9S$: 1030.3502; found 516.1817 (M+2H).

Example 6: 1-{[(octyloxy)carbonyl]oxy}ethyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate Using General procedure I with Preparation 12 and 1-octanol as the appropriate alcohol, Example 6 was obtained. HRMS calculated for $C_{58}H_{64}ClFN_6O_9S$: 1030.3502; found 538.2133 and 538.2149 (M+2H)

Example 7: 1-[(dimethylcarbamoyl)oxy]ethyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate Using General procedure II with Preparation 12 and dimethylamine hydrochloride as amine reagent applying 2.15 eq. of pyridine in Step A, Example 7 was obtained. HRMS calculated for $C_{52}H_{53}ClFN_7O_8S$: 989.3349; found 495.6740 and 495.6738 (M+2H)

Example 8: 1-[(diethylcarbamoyl)oxy]ethyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate Using General procedure II with Preparation 12 and diethylamine as amine reagent, Example 8 was obtained. HRMS calculated for $C_{54}H_{57}ClFN_7O_8S$: 1017.3662; found 509.6902 (M+2H)

Example 9: 1-{[(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoyl]oxy}ethyl morpholine-4-carboxylate Using General procedure II with Preparation 12 and morpholine as amine reagent, Example 9 was obtained. HRMS calculated for $C_{54}H_{55}ClFN_7O_9S$: 1031.3455; found 516.6826 and 516.6821 (M+2H).

Example 10: 1-{[(2-methoxyethyl)carbamoyl]oxy}ethyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl) propanoate Using General procedure II with Preparation 12 and 2-methoxyethanamine as amine reagent, Example 10 was obtained. HRMS calculated for $C_{53}H_{55}ClFN_7O_9S$: 1019.3455; found 510.6809 and 510.6813 (M+2H)

Example 11: 1-{[bis(2-methoxyethyl)carbamoyl]oxy}ethyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate Using General procedure II with Preparation 12 and 2-methoxy-N-(2-methoxyethyl)ethanamine as amine reagent, Example 11 was obtained. HRMS calculated for $C_{56}H_{61}ClFN_7O_{10}S$: 1077.3873; found 539.7029 and 539.7017 (M+2H)

Example 12: 1-{[(2-methoxy-2-oxoethyl)(methyl)carbamoyl]oxy}ethyl (2R)-2-{[(5S$_a$)-5-{3-chloro-2-methyl-4-[2-(4-methylpiperazin-1-yl)ethoxy]phenyl}-6-(4-fluorophenyl) thieno[2,3-d]pyrimidin-4-yl]oxy}-3-(2-{[2-(2-methoxyphenyl)pyrimidin-4-yl]methoxy}phenyl)propanoate Using General procedure II with Preparation 12 and methyl 2-(methylamino)acetate hydrochloride as amine reagent applying 2.15 eq. of pyridine in Step A, Example 12 was obtained. HRMS calculated for $C_{54}H_{55}ClFN_7O_{10}S$: 1047.3403; found 524.6782 and 524.6781 (M+2H).

Example 13: (phosphonooxy)methyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate 700 mg Preparation 12 (0.8 mmol), 233 mg di-tert-butyl chloromethyl phosphate (0.9 mmol), 240 mg sodium iodide (1.6 mmol) and 521 mg Cs$_2$CO$_3$ (1.6 mmol) were dissolved in 8 mL DMF and the reaction mixture was stirred at room temperature under nitrogen atmosphere until no further conversion was observed. The mixture was diluted with water and extracted with ethyl acetate. The organic layer was washed with water, dried over Na$_2$SO$_4$ and concentrated under reduced pressure. The crude product was purified via flash chromatography on silica gel using DCM and MeOH eluents to obtain the di-tert-butyl ester intermediate.

160 mg di-tert-butyl ester (0.15 mmol) was dissolved in 8 mL DCM and cooled with ice water bath. 4 mL TFA was added slowly to the mixture. After the addition of TFA the mixture was stirred for further 15 minutes and then it was concentrated under reduced pressure to obtain the crude product in salt form. Preparative HPLC using formic acid solution and ACN followed by lyophilisation resulted in Example 13 as a white solid. HRMS calculated for C$_{48}$H$_{47}$ClFN$_6$O$_{10}$PS: 984.2485; found 493.1338 (M+2H)

Example 14: 1-[(ethoxycarbonyl)oxy]ethyl (2R)-2-{[5-{2,6-dimethyl-4-[2-(4-methyl piperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate Using General procedure I with Preparation 14 and ethanol as the appropriate alcohol, Example 14 was obtained.

Example 15: 1-[(ethoxycarbonyl)oxy]ethyl (2R)-2-{[5-{3,5-dichloro-2,6-dimethyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate Using General procedure I with Preparation 13 and ethanol as the appropriate alcohol, Example 15 was obtained. HRMS calculated for C$_{53}$H$_{53}$Cl$_2$FN$_6$O$_9$S: 1038.2955; found 520.1543 and 520.1549 (M+2H)$^{2+}$ Example 16: 1-[(dimethylcarbamoyl)oxy]ethyl (2R)-2-{[5-{2,6-dimethyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate Using General procedure II with Preparation 14 and dimethylamine hydrochloride as amine reagent applying 2.15 eq. of pyridine in Step A, Example 16 was obtained.

Example 17: 1-[(dimethylcarbamoyl)oxy]ethyl (2R)-2-{[5-{3,5-dichloro-2,6-dimethyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate Using General procedure II with Preparation 13 and dimethylamine hydrochloride as amine reagent applying 2.15 eq. of pyridine in Step A, Example 17 was obtained. HRMS calculated for C$_{53}$H$_{54}$Cl$_2$FN$_7$O$_8$S: 1037.3115; found 519.6616 and 519.6632 (M+2H)$^{2+}$.

PHARMACOLOGICAL STUDY

Example A: Inhibition of Mcl-1 by the Fluorescence Polarisation Technique

The relative binding potency of each compound was determined via Fluorescence Polarisation (FP). The method utilised a Fluorescein labelled ligand (Fluorescein-βAla-Ahx-A-REIGAQLRRMADDLNAQY-OH; mw 2,765) which binds to the Mcl-1 protein (such that Mcl-1 corresponds to the UniProtKB® primary accession number: Q07820) leading to an increased anisotropy measured in milli-polarisation (mP) units using a reader. The addition of a compound which binds competitively to the same site as the ligand will result in a greater proportion of unbound ligand in the system indicated by a decrease in mP units.

An 11 point serial dilution of each compound was prepared in DMSO and 2 μl transferred into flat bottomed, low binding, 384-well plate (final DMSO concentration 5%). 38 μl of buffer (10 mM 4-(2-hydroxyethyl)-1-piperazineethanesulfonic acid [HEPES], 150 mM NaCl, 0.05% Tween 20, pH 7.4), containing the Fluorescein labelled ligand (final concentration 1 nM) and Mcl-1 protein (final concentration 5 nM) was then added.

Assay plates were incubated ~2 hours at room temperature before FP was measured on a Biomek Synergy2 reader (Ex. 528 nm, Em. 640 nm, Cut off 510 nm) and mP units calculated. The binding of increasing doses of test compound was expressed as a percentage reduction in mP compared to a window established between '5% DMSO only' and '100% inhibition' controls. 11-point dose response curves were plotted with XL-Fit software using a 4-Parameter Logistic Model (Sigmoidal Dose-Response Model) and the inhibitory concentrations that gave a 50% reduction in mP (IC$_{50}$) were determined. Results are presented in Table 1 below.

The results show that the compounds of the invention inhibit interaction between the Mcl-1 protein and the fluorescent peptide described hereinbefore.

Example B: In Vitro Cytotoxicity

The cytotoxicity studies were carried out on the H929 multiple myeloma tumour line.

The cells are distributed onto microplates and exposed to the test compounds for 48 hours.

The cell viability is then quantified by a colorimetric assay, the Microculture Tetrazolium Assay (Cancer Res., 1987, 47, 939-942).

The results are expressed in IC$_{50}$ (the concentration of compound that inhibits cell viability by 50%) and are presented in Table 1 below.

The results show that the compounds of the invention are cytotoxic.

TABLE 1

IC$_{50}$ of Mcl-1 inhibition (fluorescence polarisation test) and of cytotoxicity for H929 cells

| | IC$_{50}$ (μM) Mcl-1 FP | IC$_{50}$ (μM) MTT H929 |
|---|---|---|
| Example 1 | 0.037 | ND |
| Example 2 | 0.361 | ND |
| Example 3 | 0.292 | ND |
| Example 4 | 0.959 | ND |
| Example 5 | 0.37 | ND |
| Example 6 | 0.51 | ND |
| Example 7 | 0.438 | ND |
| Example 8 | 1.41 | ND |
| Example 9 | 0.52 | ND |
| Example 10 | 0.147 | ND |
| Example 11 | 0.551 | ND |
| Example 12 | 0.318 | ND |
| Example 13 | 0.0032 | ND |
| Example 14 | ND | ND |
| Example 15 | 0.453 | 0.068 |

TABLE 1-continued

IC$_{50}$ of Mcl-1 inhibition (fluorescence polarisation test) and of cytotoxicity for H929 cells

| | IC$_{50}$ (µM) Mcl-1 FP | IC$_{50}$ (µM) MTT H929 |
|---|---|---|
| Example 16 | ND | ND |
| Example 17 | 1.536 | 0.702 |
| Preparation 13 | 0.00181 | 0.025 |
| Preparation 14 | ND | ND |

ND: not determined

Example C: Quantification of the Cleaved Form of PARP In Vivo

The ability of the compounds of the invention to induce apoptosis, by measuring cleaved PARP levels, is evaluated in a xenograft model of AMO-1 multiple myeloma cells. $1.10^7$ AMO-1 cells are grafted sub-cutaneously into immunosuppressed mice (SCID strain). 12 to 14 days after the graft, the animals are treated by intraveinous or oral routes with the various compounds. After treatment, the tumour masses are recovered and lysed, and the cleaved form of PARP is quantified in the tumour lysates.

The quantification is carried out using the "Meso Scale Discovery (MSD) ELISA platform" test, which specifically assays the cleaved form of PARP. It is expressed in the form of an activation factor corresponding to the ratio between the quantity of cleaved PARP in the treated mice divided by the quantity of cleaved PARP in the control mice.

The results show that the compounds of the invention are capable of inducing apoptosis in AMO-1 tumour cells in vivo.

Example D: Anti-Tumour Activity In Vivo

The anti-tumour activity of the compounds of the invention is evaluated in a xenograft model of AMO-1 multiple myeloma cells.

$1\times10^7$ AMO-1 cells are grafted sub-cutaneously into immunosuppressed mice (SCID strain).

6 to 8 days after the graft, when the tumour mass has reached about 150 mm$^3$, the mice are treated with the various compounds in a daily schedule (5-day treatment). The tumour mass is measured twice weekly from the start of treatment.

The results obtained using ΔT/C ratio (i.e. qualification parameter of the activity of a product, which is defined as the ratio tumour volume of the treated group/tumour volume of the untreated control group) show that the compounds of the invention induce significant tumour regression during the treatment period.

Example E: Pharmaceutical Composition: Tablets 1000 tablets containing a dose of 5 mg of a compound selected from Examples 1 to 17 and Preparations 13 and 14 . . . 5 g
Wheat starch . . . 20 g
Maize starch . . . 20 g
Lactose . . . 30 g
Magnesium stearate . . . 2 g
Silica . . . 1 g
Hydroxypropylcellulose . . . 2 g

The invention claimed is:
1. A compound of formula (I):

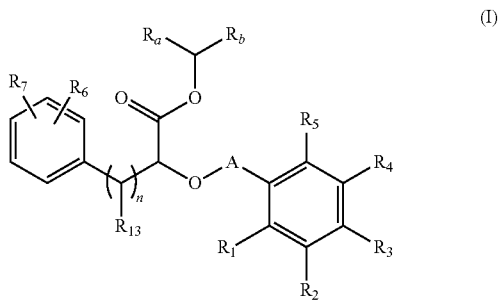

wherein:
represents the group

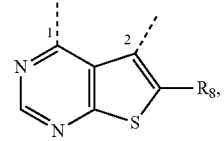

wherein 1 is linked to the oxygen atom and 2 is linked to the phenyl ring,

R$_1$ represents a linear or branched (C$_1$-C$_6$)alkyl group, a linear or branched (C$_2$-C$_6$)alkenyl group, a linear or branched (C$_2$-C$_6$)alkynyl group, a linear or branched (C$_1$-C$_6$)alkoxy group, a —S—(C$_1$-C$_6$)alkyl group, a linear or branched (C$_1$-C$_6$)polyhaloalkyl, a hydroxy group, a hydroxy(C$_1$-C$_6$)alkyl group, a cyano group, —NR$_{11}$R$_{11}$', —Cy$_6$, or a halogen atom, R$_2$, R$_3$, R$_4$ and R$_5$ independently of one another represent a hydrogen atom, a halogen atom, a linear or branched (C$_1$-C$_6$)alkyl group, a linear or branched (C$_2$-C$_6$)alkenyl group, a linear or branched (C$_2$-C$_6$)alkynyl group, a linear or branched (C$_1$-C$_6$)polyhaloalkyl, a hydroxy group, a hydroxy(C$_1$-C$_6$)alkyl group, a linear or branched (C$_1$-C$_6$)alkoxy group, a —S—(C$_1$-C$_6$)alkyl group, a cyano group, a nitro group, -alkyl(C$_0$-C$_6$)—NR$_9$R$_9$', —O-alkyl(C$_1$-C$_6$)—NR$_9$R$_9$', —O-alkyl(C$_1$-C$_6$)—R$_{10}$, —C(O)—OR$_9$, —O—C(O)—R$_9$, —C(O)—NR$_9$R$_9$', —NR$_9$—C(O)—R$_9$', —NR$_9$—C(O)—OR$_9$', -alkyl(C$_1$-C$_6$)—NR$_9$—C(O)—R$_9$', —SO$_2$—NR$_9$R$_9$', —SO$_2$-alkyl(C$_1$-C$_6$), or the substituents of one of the pairs (R$_2$, R$_3$), (R$_3$, R$_4$), (R$_4$, R$_5$), when grafted onto two adjacent carbon atoms, together with the carbon atoms carrying them, form an aromatic or non-aromatic ring having from 5 to 7 ring members, which ring may contain from 1 to 3 heteroatoms selected from oxygen, sulphur and nitrogen, wherein the resulting ring may be substituted by a group selected from the group consisting of a linear or branched (C$_1$-C$_6$)alkyl group, —NR$_{11}$R$_{11}$', -alkyl(C$_0$-C$_6$)—Cy$_1$, and oxo, R$_6$ and R$_7$ independently of one another represent a hydrogen atom, a halogen atom, a linear or branched (C$_1$-C$_6$)alkyl group, a linear or branched (C$_2$-C$_6$)alkenyl group, a linear or branched (C$_2$-C$_6$)alkynyl group, a linear or branched (C$_1$-C$_6$)polyhaloalkyl, a hydroxy group, a linear or branched (C$_1$-C$_6$)alkoxy group, a —S—(C$_1$-C$_6$)alkyl group, a cyano group, a nitro group, -alkyl(C$_0$-C$_6$)—NR$_9$R$_9$', —O-alkyl(C$_1$-C$_6$)—NR$_9$R$_9$', —O—Cy$_1$, -alkyl(C$_0$-C$_6$)—Cy$_1$, -alkenyl(C$_2$-C$_6$)—Cy$_1$, -alkynyl(C$_2$-C$_6$)—Cy$_1$, —O-alkyl(C$_1$-C$_6$)—R$_{10}$, —C(O)—OR$_9$, —O—C(O)—R$_9$, —C(O)—NR$_9$R$_9$',
—NR$_9$—C(O)—R$_9$', —NR$_9$—C(O)—OR$_9$', -alkyl(C$_1$-C$_6$)—NR$_9$—C(O)—R$_9$', —SO$_2$—NR$_9$R$_9$', —SO$_2$-alkyl(C$_1$-C$_6$), or the substituents of the pair (R$_6$, R$_7$), when grafted onto two adjacent carbon atoms, together with the carbon atoms carrying them, form an aromatic or non-aromatic ring having from 5 to 7 ring members, which ring may contain from 1 to 3 heteroatoms selected from oxygen, sulphur and nitrogen, wherein the resulting ring may be substituted by a group selected from the group consisting of a linear or branched (C$_1$-C$_6$)alkyl group, —NR$_{11}$R$_{11}$', -alkyl(C$_0$-C$_6$)-Cy$_1$, and oxo, R$_8$ represents a linear or branched (C$_1$-C$_6$)alkyl group, a linear or branched (C$_2$-C$_6$)alkenyl group, a linear or branched (C$_2$-C$_6$)alkynyl group, —Cy$_3$, -alkyl(C$_1$-C$_6$)—Cy$_3$, -alkenyl(C$_2$-C$_6$)—Cy$_3$, -alkynyl(C$_2$-C$_6$)—Cy$_3$, —Cy$_3$-Cy$_4$, -alkynyl(C$_2$-C$_6$)—O—Cy$_3$, —Cy$_3$-alkyl(C$_0$-C$_6$)—O-alkyl(C$_0$-C$_6$)—Cy$_4$, a halogen atom, a cyano group, —C(O)—R$_{12}$, or —C(O)—NR$_{12}$R$_{12}$', R$_9$ and R$_9$' independently of one another represent a hydrogen atom, a linear or branched (C$_1$-C$_6$)alkyl group, -alkyl(C$_0$-C$_6$)—Cy$_1$, or the substituents of the pair (R$_9$, R$_9$'), together with the nitrogen atom carrying them, form an aromatic or non-aromatic ring having from 5 to 7 ring members, which ring may contain, in addition to the nitrogen atom, from 1 to 3 heteroatoms selected from oxygen, sulphur and nitrogen, wherein the nitrogen may be substituted by a hydrogen atom or a linear or branched (C$_1$-C$_6$)alkyl group and wherein one or more of the carbon atoms of the possible substituents, may be deuterated, R$_{10}$ represents —Cy$_1$, —Cy$_1$-alkyl(C$_0$-C$_6$)—Cy$_2$, —Cy$_1$-alkyl(C$_0$-C$_6$)—O-alkyl(C$_0$-C$_6$)—Cy$_2$, —Cy$_1$-alkyl(C$_0$-C$_6$)—NR$_9$-alkyl(C$_0$-C$_6$)—Cy$_2$, —Cy$_1$-Cy$_2$-O-alkyl(C$_0$-C$_6$)—Cy$_5$, —C(O)—NR$_9$R$_9$', —NR$_9$R$_9$', —OR$_9$, —NR$_9$—C(O)—R$_9$', —O-alkyl(C$_1$-C$_6$)—OR$_9$, —SO$_2$—R$_9$, —C(O)—OR$_9$, or —NH—C(O)—NH—R$_7$, R$_{11}$, R$_{11}$', R$_{12}$ and R$_{12}$', independently of one another represent a hydrogen atom or an optionally substituted linear or branched (C$_1$-C$_6$)alkyl group, R$_{13}$ represents a hydrogen atom, a hydroxy group, or a hydroxy(C$_1$-C$_6$)alkyl group, R$_a$ represents a hydrogen atom or a linear or branched (C$_1$-C$_6$)alkyl group, R$_b$ represents a —O—C(O)—O—R$_c$ group, a —O—C(O)—NR$_c$R$_c$' group, or a —O—P(O)(OR$_c$)$_2$ group, R$_c$ and R$_c$' independently of one another represent a hydrogen atom, a linear or branched (C$_1$-C$_8$)alkyl group, a cycloalkyl group, a (C$_1$-C$_6$)alkoxy(C$_1$-C$_6$)alkyl group, or a (C$_1$-C$_6$)alkoxycarbonyl(C$_1$-C$_6$)alkyl group, or the substituents of the pair (R$_c$, R$_c$'), together with the nitrogen atom carrying them, form a non-aromatic ring having from 5 to 7 ring members, which ring may contain, in addition to the nitrogen atom, from 1 to 3 heteroatoms selected from oxygen and nitrogen, wherein the nitrogen may be substituted by a linear or branched (C$_1$-C$_6$)alkyl group, Cy$_1$, Cy$_2$, Cy$_3$, Cy$_4$, Cy$_5$ and Cy$_6$, independently of one another, represent a cycloalkyl group, a heterocycloalkyl group, an aryl group or a heteroaryl group, n is an integer equal to 0 or 1, wherein:
"aryl" means a phenyl, naphthyl, biphenyl, indanyl or indenyl group,
"heteroaryl" means any mono- or bi-cyclic group composed of from 5 to 10 ring members, having at least one aromatic moiety and containing from 1 to 3 heteroatoms selected from oxygen, sulphur and nitrogen,
"cycloalkyl" means any mono- or bi-cyclic non-aromatic carbocyclic group containing from 3 to 10 ring members,
"heterocycloalkyl" means any mono- or bi-cyclic non-aromatic carbocyclic group containing from 3 to 10 ring members, and containing from 1 to 3 heteroatoms selected from oxygen, sulphur and nitrogen, which may include fused, bridged or spiro ring systems,
wherein the aryl, heteroaryl, cycloalkyl and heterocycloalkyl groups so defined and the alkyl, alkenyl, alkynyl, alkoxy groups, may be substituted by from 1 to 4 groups selected from linear or branched (C$_1$-C$_6$)alkyl, linear or branched (C$_2$-C$_6$)alkenyl group, linear or branched (C$_2$-C$_6$) alkynyl group, linear or branched (C$_1$-C$_6$)alkoxy, (C$_1$-C$_6$) alkyl-S—, hydroxy, oxo (or N-oxide where appropriate), nitro, cyano, —C(O)—OR', —O—C(O)—R', —C(O)—NR'R", —NR'R", —(C=NR')—OR", linear or branched (C$_1$-C$_6$)polyhaloalkyl, trifluoromethoxy, or halogen, wherein R' and R", independently of one another, represent a hydrogen atom or a linear or branched (C$_1$-C$_6$)alkyl group, and wherein one or more of the carbon atoms of the preceding possible substituents, may be deuterated, its enantiomers, diastereoisomers and atropisomers, or a pharmaceutically acceptable salt thereof.

2. The compound according to claim 1, wherein at least one of the groups selected from R$_2$, R$_3$, R$_4$ and R$_5$ does not represent a hydrogen atom.

3. The compound according to claim 1, wherein n is an integer equal to 1.

4. The compound according to claim 1, wherein R$_1$ represents a linear or branched (C$_1$-C$_6$)alkyl group or a halogen atom.

5. The compound according to claim 1, wherein R$_{13}$ represents a hydrogen atom.

6. The compound according to claim 1, wherein R$_4$ and R$_5$ each represent a hydrogen atom.

7. The compound according to claim 1, wherein

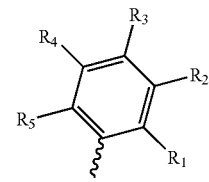

represents

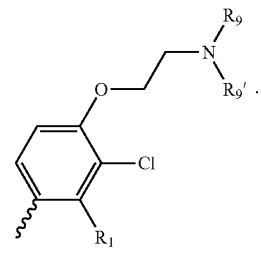

8. The compound according to claim 1, wherein

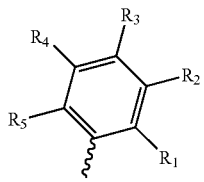

represents

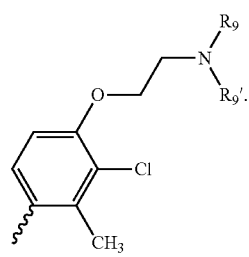

9. The compound according to claim 1, wherein the substituents of the pair ($R_1$, $R_5$) are identical and the substituents of the pair ($R_2$, $R_4$) are identical.

10. The compound according to claim 1, wherein $R_6$ represents an optionally substituted linear or branched ($C_1$-$C_6$)alkoxy group or a —O-alkyl($C_1$-$C_6$)—$R_{10}$ group.

11. The compound according to claim 1, wherein $R_7$ represents a hydrogen atom.

12. The compound according to claim 1, wherein

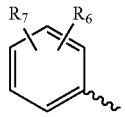

represents

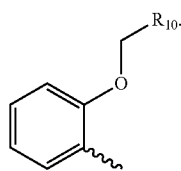

13. The compound according to claim 1, wherein $R_8$ represents a linear or branched ($C_1$-$C_6$)alkyl group, a linear or branched ($C_2$-$C_6$)alkenyl group, a linear or branched ($C_2$-$C_6$)alkynyl group, an aryl group or a heteroaryl group.

14. The compound according to claim 1, wherein $R_9$ and $R_9'$, independently of one another, represent a linear or branched ($C_1$-$C_6$)alkyl group, or the substituents of the pair ($R_9$, $R_9'$), together with the nitrogen atom carrying them, form a non-aromatic ring having from 5 to 7 ring members, which ring may contain, in addition to the nitrogen atom, from 1 to 3 heteroatoms selected from oxygen, sulphur and nitrogen, wherein the nitrogen may be substituted by a hydrogen atom or a linear or branched ($C_1$-$C_6$)alkyl group.

15. The compound according to claim 1, wherein $R_{10}$ represents —$Cy_1$, —$Cy_1$-alkyl($C_0$-$C_6$)—O-alkyl($C_0$-$C_6$)—$Cy_2$ or —$Cy_1$-alkyl($C_0$-$C_6$)-$Cy_2$.

16. The compound according to claim 1, wherein $Cy_1$ represents a heteroaryl group.

17. The compound according to claim 1, wherein $Cy_2$ represents a phenyl group, a pyridinyl group, a pyrazolyl group, a morpholinyl group, a furanyl group or a cyclopropyl group.

18. The compound according to claim 1, wherein $R_{10}$ represents —$Cy_1$-$Cy_2$, wherein $Cy_1$ represents a pyrimidinyl group and $Cy_2$ represents a phenyl group, a pyridinyl group, a pyrazolyl group, a morpholinyl group, a furanyl group, or a cyclopropyl group.

19. The compound according to claim 1, wherein $R_a$ represents a hydrogen atom or a methyl group.

20. The compound according to claim 1, wherein $R_b$ represents a —O—C(O)—O—($C_1$-$C_8$)alkyl group; a —O—C(O)—O-cycloalkyl group; a —O—C(O)—$NR_cR_c'$ group, wherein $R_c$ and $R_c'$, independently of one another, represent a hydrogen atom, a linear or branched ($C_1$-$C_8$)alkyl group, a ($C_1$-$C_6$)alkoxy($C_1$-$C_6$)alkyl group, a ($C_1$-$C_6$)alkoxycarbonyl($C_1$-$C_6$)alkyl group, or the substituents of the pair ($R_c$, $R_c'$), together with the nitrogen atom carrying them, form a non-aromatic ring having from 5 to 7 ring members, which ring may contain, in addition to the nitrogen atom, from 1 to 3 heteroatoms selected from oxygen and nitrogen; or a —O—P(O)(OH)$_2$ group.

21. The compound according to claim 1, which is selected from the group consisting of:

1-[(methoxycarbonyl)oxy]ethyl (2R)-2-{[(5$S_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate;

1-[(ethoxycarbonyl)oxy]ethyl (2R)-2-{[(5$S_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate;

1-{[(propan-2-yloxy)carbonyl]oxy}ethyl (2R)-2-{[(5$S_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl) propanoate;

1-[(tert-butoxycarbonyl)oxy]ethyl (2R)-2-{[(5$S_0$)-5-{3-chloro-2-methyl-4-[2-(4-methylpiperazin-1-yl)ethoxy]phenyl)-6-(4-fluorophenyl)thieno[2,3-d]pyrimidin-4-yl]oxy}-3-(2-{[2-(2-methoxyphenyl)pyrimidin-4-yl]methoxy}phenyl)propanoate;

1-{[(cyclopentyloxy)carbonyl]oxy}ethyl (2R)-2-{[(5$S_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl) propanoate;

1-{[((octyloxy)carbonyl]oxy}ethyl (2R)-2-{[(5$S_a$)-5-{3-chloro-2-methyl-4-[2-(4-methylpiperazin-1-yl)ethoxy]phenyl)-6-(4-fluorophenyl)thieno[2,3-d]pyrimidin-4-yl]oxy}-3-(2-{[2-(2-methoxyphenyl)pyrimidin-4-yl]methoxy}phenyl)propanoate;

1-[(dimethylcarbamoyl)oxy]ethyl (2R)-2-{[(5$S_a$)—S-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate;

1-[(diethylcarbamoyl)oxy]ethyl (2R)-2-{[(5$S_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate;

1-{[(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoyl]oxy}ethyl morpholine-4-carboxylate;

1-{[(2-methoxyethyl)carbamoyl]oxy}ethyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl) propanoate;

1-{[bis(2-methoxyethyl)carbamoyl]oxy}ethyl (2R)-2-{[(5S$_a$)-5-{3-chloro-2-methyl-4-[2-(4-methylpiperazin-1 yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate;

1-{[(2-methoxy-2-oxoethyl)(methyl)carbamoyl]oxy}ethyl (2R)-2-{[(5S$_a$)-5-{3-chloro-2-methyl-4-[2-(4-methylpiperazin-1-yl)ethoxy]phenyl}-6-(4-fluoro phenyl)thieno[2,3-d]pyrimidin-4-yl]oxy}-3-(2-{[2-(2-methoxyphenyl)pyrimidin-4-yl]methoxy}phenyl)propanoate;

(phosphonooxy)methyl (2R)-2-{[(5S$_a$)-5-{3-chloro-2-methyl-4-[2-(4-methyl piperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate;

1-[(ethoxycarbonyl)oxy]ethyl (2R)-2-{[5-{2,6-dimethyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate;

1-[(ethoxycarbonyl)oxy]ethyl (2R)-2-{[5-{3,5-dichloro-2,6-dimethyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate;

1-[(dimethylcarbamoyl)oxy]ethyl (2R)-2-{[5-{2,6-dimethyl-4-[2-(4-methyl piperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate; and 1-[(dimethylcarbamoyl)oxy]ethyl (2R)-2-{[5-{3,5-dichloro-2,6-dimethyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate.

22. A compound of formula (VI$_A$):

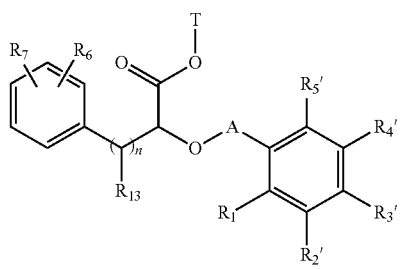

(VI$_A$)

wherein:

$R_2'$, $R_3'$, $R_4'$ and $R_5'$ independently of one another represent a halogen atom, a linear or branched ($C_1$-$C_6$)alkyl group, a linear or branched ($C_2$-$C_6$)alkenyl group, a linear or branched ($C_2$-$C_6$)alkynyl group, a linear or branched ($C_1$-$C_6$)polyhaloalkyl, a hydroxy group, a hydroxy($C_1$-$C_6$)alkyl group, a linear or branched ($C_1$-$C_6$)alkoxy group, a —S—($C_1$-$C_6$)alkyl group, a cyano group, a nitro group, -alkyl($C_0$-$C_6$)—NR$_9$R$_9$', —O-alkyl($C_1$-$C_6$)—NR$_9$R$_9$', —O-alkyl($C_1$-$C_6$)—R$_{10}$, —C(O)—OR$_9$, —O—C(O)—R$_9$, —C(O)—NR$_9$R$_9$', —NR$_9$—C(O)—R$_9$', —NR$_9$—C(O)—OR$_9$', -alkyl($C_1$-$C_6$)—NR$_9$—C(O)—R$_9$', —SO$_2$—NR$_9$R$_9$', —SO$_2$-alkyl($C_1$-$C_6$), T represents a ($C_1$-$C_6$)alkyl group, a ($C_1$-$C_6$)carbonyloxy ($C_1$-$C_6$)alkyl group or a di($C_1$-$C_6$)alkylaminocarbonyl ($C_1$-$C_6$)alkyl group, A represents the group

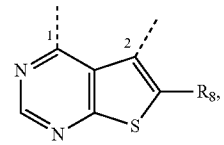

wherein 1 is linked to the oxygen atom and 2 is linked to the phenyl ring, $R_1$ represents a linear or branched ($C_1$-$C_6$)alkyl group, a linear or branched ($C_2$-$C_6$)alkenyl group, a linear or branched ($C_2$-$C_6$)alkynyl group, a linear or branched ($C_1$-$C_6$)alkoxy group, a —S—($C_1$-$C_6$)alkyl group, a linear or branched ($C_1$-$C_6$)polyhaloalkyl, a hydroxy group, a hydroxy($C_1$-$C_6$)alkyl group, a cyano group, —NR$_{11}$R$_{11}$', —Cy$_6$, or a halogen atom, $R_6$ and $R_7$ independently of one another represent a hydrogen atom, a halogen atom, a linear or branched ($C_1$-$C_6$)alkyl group, a linear or branched ($C_2$-$C_6$)alkenyl group, a linear or branched ($C_2$-$C_6$)alkynyl group, a linear or branched ($C_1$-$C_6$)polyhaloalkyl, a hydroxy group, a linear or branched ($C_1$-$C_6$)alkoxy group, a —S—($C_1$-$C_6$)alkyl group, a cyano group, a nitro group, -alkyl($C_0$-$C_6$)—NR$_9$R$_9$', —O-alkyl($C_1$-$C_6$)—NR$_9$R$_9$', —O—Cy$_1$, -alkyl($C_0$-$C_6$)—Cy$_1$, -alkenyl($C_2$-$C_6$)—Cy$_1$, -alkynyl($C_2$-$C_6$)—Cy$_1$, —O-alkyl($C_1$-$C_6$)—R$_{10}$, —C(O)—OR$_9$, —O—C(O)—R$_9$, —C(O)—NR$_9$R$_9$', —NR$_9$—C(O)—R$_9$', —NR$_9$—C(O)—OR$_9$', -alkyl($C_1$-$C_6$)—NR$_9$—C(O)—R$_9$', —SO$_2$—NR$_9$R$_9$', —SO$_2$-alkyl($C_1$-$C_6$), or the substituents of the pair ($R_6$, $R_7$), when grafted onto two adjacent carbon atoms, together with the carbon atoms carrying them, form an aromatic or non-aromatic ring having from 5 to 7 ring members, which ring may contain from 1 to 3 heteroatoms selected from oxygen, sulphur and nitrogen, wherein the resulting ring may be substituted by a group selected from the group consisting of a linear or branched ($C_1$-$C_6$)alkyl group, —NR$_{11}$R$_{11}$', -alkyl($C_0$-$C_6$)—Cy$_1$, and oxo, $R_8$ represents a linear or branched ($C_1$-$C_6$)alkyl group, a linear or branched ($C_2$-$C_6$)alkenyl group, a linear or branched ($C_2$-$C_6$)alkynyl group, —Cy$_3$, -alkyl($C_1$-$C_6$)—Cy$_3$, -alkenyl($C_2$-$C_6$)—Cy$_3$, -alkynyl($C_2$-$C_6$)—Cy$_3$, —Cy$_3$-Cy$_4$, -alkynyl($C_2$-$C_6$)—O—Cy$_3$, —Cy$_3$-alkyl($C_0$-$C_6$)—O-alkyl($C_0$-$C_6$)—Cy$_4$, a halogen atom, a cyano group, —C(O)—R$_{12}$, or —C(O)—NR$_{12}$R$_{12}$', $R_9$ and $R_9$' independently of one another represent a hydrogen atom, a linear or branched ($C_1$-$C_6$)alkyl group, -alkyl($C_0$-$C_6$)—Cy$_1$, or the substituents of the pair ($R_9$, $R_9$'), together with the nitrogen atom carrying them, form an aromatic or non-aromatic ring having from 5 to 7 ring members, which ring may contain, in addition to the nitrogen atom, from 1 to 3 heteroatoms selected from oxygen, sulphur and nitrogen, wherein the nitrogen may be substituted by a hydrogen atom or a linear or branched $(C_1-C_6)$alkyl group and wherein one or more of the carbon atoms of the possible substituents, may be deuterated, $R_{10}$ represents —$Cy_1$, —$Cy_1$-alkyl$(C_0-C_6)$—$Cy_2$, —$Cy_1$-alkyl$(C_0-C_6)$—O-alkyl$(C_0-C_6)$—$Cy_2$, —$Cy_1$-alkyl$(C_0-C_6)$—$NR_9$-alkyl$(C_0-C_6)$—$Cy_2$, —$Cy_1$-$Cy_2$-O-alkyl$(C_0-C_6)$—$Cy_5$, —C(O)—$NR_9R_9'$, —$NR_9R_9'$, —$OR_9$, —$NR_9$—C(O)—$R_9'$, —O-alkyl$(C_1-C_6)$—$OR_9$, —$SO_2$—$R_9$, —C(O)—$OR_9$, or —NH—C(O)—NH—$R_7$, $R_{10}$, $R_{11}'$, $R_{12}$ and $R_{12}'$, independently of one another represent a hydrogen atom or an optionally substituted linear or branched $(C_1-C_6)$alkyl group, $R_{13}$ represents a hydrogen atom, a hydroxy group, or a hydroxy$(C_1-C_5)$alkyl group, $Cy_1$, $Cy_2$, $Cy_3$, $Cy_4$, $Cy_5$ and $Cy_6$, independently of one another, represent a cycloalkyl group, a heterocycloalkyl group, an aryl group or a heteroaryl group, and n is an integer equal to 0 or 1, wherein:

"aryl" means a phenyl, naphthyl, biphenyl, indanyl or indenyl group,

"heteroaryl" means any mono- or bi-cyclic group composed of from 5 to 10 ring members, having at least one aromatic moiety and containing from 1 to 3 heteroatoms selected from oxygen, sulphur and nitrogen, "cycloalkyl" means any mono- or bi-cyclic non-aromatic carbocyclic group containing from 3 to 10 ring members, "heterocycloalkyl" means any mono- or bi-cyclic non-aromatic carbocyclic group containing from 3 to 10 ring members, and containing from 1 to 3 heteroatoms selected from oxygen, sulphur and nitrogen, which may include fused, bridged or spiro ring systems, wherein the aryl, heteroaryl, cycloalkyl and heterocycloalkyl groups so defined and the alkyl, alkenyl, alkynyl, alkoxy groups, may be substituted by from 1 to 4 groups selected from linear or branched $(C_1-C_6)$alkyl, linear or branched $(C_2-C_6)$alkenyl group, linear or branched $(C_2-C_6)$alkynyl group, linear or branched $(C_1-C_6)$alkoxy, $(C_1-C_6)$alkyl-S—, hydroxy, oxo (or N-oxide where appropriate), nitro, cyano, —C(O)—OR', —O—C(O)—R', —C(O)—NR'R", —NR'R", —(C=NR')—OR", linear or branched $(C_1-C_6)$polyhaloalkyl, trifluoromethoxy, or halogen, wherein R' and R", independently of one another, represent a hydrogen atom or a linear or branched $(C_1-C_6)$alkyl group, and wherein one or more of the carbon atoms of the preceding possible substituents, may be deuterated, its enantiomers, diastereoisomers or a pharmaceutically acceptable salt thereof.

23. The compound according to claim 22, wherein the substituents of the pair ($R_1$, $R_5'$) are identical and the substituents of the pair ($R_2'$, $R_4'$) are identical.

24. A compound of formula ($VII_A$):

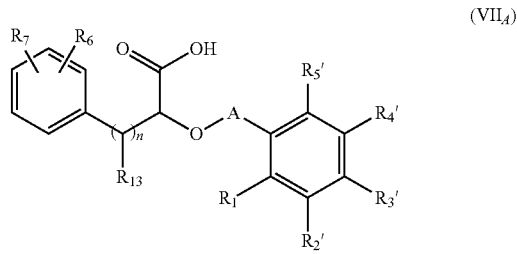

(VII$_A$)

wherein:

$R_2'$, $R_3'$, $R_4'$ and $R_5'$ independently of one another represent a halogen atom, a linear or branched $(C_1-C_6)$alkyl group, a linear or branched $(C_2-C_6)$alkenyl group, a linear or branched $(C_2-C_6)$alkynyl group, a linear or branched $(C_1-C_6)$polyhaloalkyl, a hydroxy group, a hydroxy$(C_1-C_6)$alkyl group, a linear or branched $(C_1-C_6)$alkoxy group, a —S—$(C_1-C_6)$alkyl group, a cyano group, a nitro group, -alkyl$(C_0-C_6)$—$NR_9R_9'$, —O-alkyl$(C_1-C_6)$—$NR_9R_9'$, —O-alkyl$(C_1-C_6)$—$R_{10}$, —C(O)—$OR_9$, —O—C(O)—$R_9$, —C(O)—$NR_9R_9'$, —$NR_9$—C(O)—$R_9'$, —$NR_9$—C(O)—$OR_9'$, -alkyl$(C_1-C_6)$—$NR_9$—C(O)—$R_9'$, —$SO_2$—$NR_9R_9'$, —$SO_2$-alkyl$(C_1-C_6)$, A represents the group N

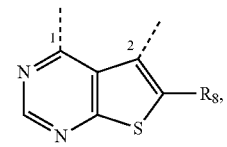

wherein 1 is linked to the oxygen atom and 2 is linked to the phenyl ring, $R_1$ represents a linear or branched $(C_1-C_6)$alkyl group, a linear or branched $(C_2-C_6)$alkenyl group, a linear or branched $(C_2-C_6)$alkynyl group, a linear or branched $(C_1-C_6)$alkoxy group, a —S—$(C_1-C_6)$alkyl group, a linear or branched $(C_1-C_6)$polyhaloalkyl, a hydroxy group, a hydroxy$(C_1-C_6)$alkyl group, a cyano group, —$NR_{11}R_{11}'$, —$Cy_6$, or a halogen atom, $R_6$ and $R_7$ independently of one another represent a hydrogen atom, a halogen atom, a linear or branched $(C_1-C_6)$alkyl group, a linear or branched $(C_2-C_6)$alkenyl group, a linear or branched $(C_2-C_6)$alkynyl group, a linear or branched $(C_1-C_6)$polyhaloalkyl, a hydroxy group, a linear or branched $(C_1-C_6)$alkoxy group, a —S—$(C_1-C_6)$alkyl group, a cyano group, a nitro group, -alkyl$(C_0-C_6)$—$NR_9R_9'$, —O-alkyl$(C_1-C_6)$—$NR_9R_9'$, —O—$Cy_1$, -alkyl$(C_0-C_6)$—$Cy_1$, -alkenyl$(C_2-C_6)$—$Cy_1$, -alkynyl$(C_2-C_6)$—$Cy_1$, —O-alkyl$(C_1-C_6)$—$R_{10}$, —C(O)—$OR_9$, —O—C(O)—$R_9$, —C(O)—$NR_9R_9'$, —$NR_9$—C(O)—$R_9'$, —$NR_9$—C(O)—$OR_9'$, -alkyl$(C_1-C_6)$—$NR_9$—C(O)—$R_9'$, —$SO_2$—$NR_9R_9'$, —$SO_2$-alkyl$(C_1-C_6)$, or the substituents of the pair ($R_6$, $R_7$), when grafted onto two adjacent carbon atoms, together with the carbon atoms carrying them, form an aromatic or non-aromatic ring having from 5 to 7 ring members, which ring may contain from 1 to 3 heteroatoms selected from oxygen, sulphur and nitrogen, wherein the resulting ring may be substituted by a group selected from the group consisting of a linear or branched ($C_1$-$C_6$)alkyl group, —$NR_{11}R_{11}'$, -alkyl($C_0$-$C_6$)—$Cy_1$, and oxo, $R_8$ represents a linear or branched ($C_1$-$C_6$)alkyl group, a linear or branched ($C_2$-$C_6$)alkenyl group, a linear or branched ($C_2$-$C_6$)alkynyl group, —$Cy_3$, -alkyl($C_1$-$C_6$)—$Cy_3$, -alkenyl($C_2$-$C_6$)—$Cy_3$, -alkynyl($C_2$-$C_6$)—$Cy_3$, —$Cy_3$-$Cy_4$, -alkynyl($C_2$-$C_6$)—O—$Cy_3$, —$Cy_3$-alkyl($C_0$-$C_6$)—O-alkyl($C_0$-$C_6$)—$Cy_4$, a halogen atom, a cyano group, —C(O)—$R_{12}$, or —C(O)—$NR_{12}R_{12}'$, $R_9$ and $R_9'$ independently of one another represent a hydrogen atom, a linear or branched ($C_1$-$C_6$)alkyl group, -alkyl($C_0$-$C_6$)—$Cy_1$, or the substituents of the pair ($R_9$, $R_9'$), together with the nitrogen atom carrying them, form an aromatic or non-aromatic ring having from 5 to 7 ring members, which ring may contain, in addition to the nitrogen atom, from 1 to 3 heteroatoms selected from oxygen, sulphur and nitrogen, wherein the nitrogen may be substituted by a hydrogen atom or a linear or branched ($C_1$-$C_6$)alkyl group and wherein one or more of the carbon atoms of the possible substituents, may be deuterated, $R_{10}$ represents —$Cy_1$, —$Cy_1$-alkyl($C_0$-$C_6$)—$Cy_2$, —$Cy_1$-alkyl($C_0$-$C_6$)—O-alkyl($C_0$-$C_6$)—$Cy_2$, —$Cy_1$-alkyl($C_0$-$C_6$)—$NR_9$-alkyl($C_0$-$C_6$)—$Cy_2$, —$Cy_1$-$Cy_2$-O-alkyl($C_0$-$C_6$)—$Cy_5$, —C(O)—$NR_9R_9'$, —$NR_9R_9'$, —$OR_9$, —$NR_9$—C(O)—$R_9'$, —O-alkyl($C_1$-$C_6$)—$OR_9$, —$SO_2$—$R_9$, —C(O)—$OR_9$, or —NH—C(O)—NH—$R_7$, $R_{11}$, $R_{11}'$, $R_{12}$ and $R_{12}'$, independently of one another represent a hydrogen atom or an optionally substituted linear or branched ($C_1$-$C_6$)alkyl group, $R_{13}$ represents a hydrogen atom, a hydroxy group, or a hydroxy($C_1$-$C_6$)alkyl group, $Cy_1$, $Cy_2$, $Cy_3$, $Cy_4$, $Cy_5$ and $Cy_6$, independently of one another, represent a cycloalkyl group, a heterocycloalkyl group, an aryl group or a heteroaryl group, and n is an integer equal to 0 or 1, wherein:

"aryl" means a phenyl, naphthyl, biphenyl, indanyl or indenyl group,

"heteroaryl" means any mono- or bi-cyclic group composed of from 5 to 10 ring members, having at least one aromatic moiety and containing from 1 to 3 heteroatoms selected from oxygen, sulphur and nitrogen, "cycloalkyl" means any mono- or bi-cyclic non-aromatic carbocyclic group containing from 3 to 10 ring members, "heterocycloalkyl" means any mono- or bi-cyclic non-aromatic carbocyclic group containing from 3 to 10 ring members, and containing from 1 to 3 heteroatoms selected from oxygen, sulphur and nitrogen, which may include fused, bridged or spiro ring systems, wherein the aryl, heteroaryl, cycloalkyl and heterocycloalkyl groups so defined and the alkyl, alkenyl, alkynyl, alkoxy groups, may be substituted by from 1 to 4 groups selected from linear or branched ($C_1$-$C_6$)alkyl, linear or branched ($C_2$-$C_6$)alkenyl group, linear or branched ($C_2$-$C_6$) alkynyl group, linear or branched ($C_1$-$C_6$)alkoxy, ($C_1$-$C_6$) alkyl-S—, hydroxy, oxo (or N-oxide where appropriate), nitro, cyano, —C(O)—OR', —O—C(O)—R', —C(O)—NR'R", —NR'R", —(C═NR')—OR", linear or branched ($C_1$-$C_6$)polyhaloalkyl, trifluoromethoxy, or halogen, wherein R' and R", independently of one another, represent a hydrogen atom or a linear or branched ($C_1$-$C_6$)alkyl group, and wherein one or more of the carbon atoms of the preceding possible substituents, may be deuterated, its enantiomers, diastereoisomers and atropisomers, or a pharmaceutically acceptable salt thereof.

25. The compound according to claim 24, wherein the substituents of the pair ($R_1$, $R_5'$) are identical and the substituents of the pair ($R_2'$, $R_4'$) are identical.

26. The compound according to claim 25, which is (2R)-2-{[5-{3,5-dichloro-2,6-dimethyl-4-[2-(4-methylpiperazin 1-yl)ethoxy]phenyl}-6-(4-fluoro phenyl)thieno[2,3-d]pyrimidin-4-yl]oxy}-3-(2-{[2-(2-methoxyphenyl)pyrimidin-4-yl]methoxy}phenyl)propanoic acid.

27. A compound of formula ($VI_B$):

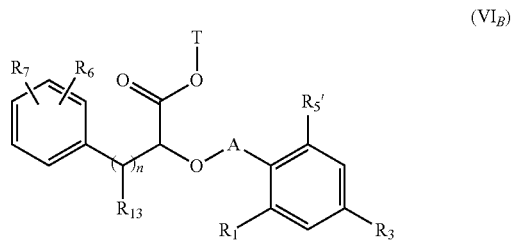

wherein:

$R_5'$ represents a halogen atom, a linear or branched ($C_1$-$C_6$)alkyl group, a linear or branched ($C_2$-$C_6$)alkenyl group, a linear or branched ($C_2$-$C_6$)alkynyl group, a linear or branched ($C_1$-$C_6$)polyhaloalkyl, a hydroxy group, a hydroxy($C_1$-$C_6$)alkyl group, a linear or branched ($C_1$-$C_6$)alkoxy group, a —S—($C_1$-$C_6$)alkyl group, a cyano group, a nitro group, -alkyl($C_0$-$C_6$)—$NR_9R_9'$, —O-alkyl($C_1$-$C_6$)—$NR_9R_9'$, —O-alkyl($C_1$-$C_6$)—$R_{10}$, —C(O)—$OR_9$, —O—C(O)—$R_9$, —C(O)—$NR_9R_9'$, —$NR_9$—C(O)—$R_9'$, —$NR_9$—C(O)—$OR_9'$, -alkyl($C_1$-$C_6$)—$NR_9$—C(O)—$R_9'$, —$SO_2$—$NR_9R_9'$, —$SO_2$-alkyl($C_1$-$C_6$), T represents a ($C_1$-$C_6$)alkyl group, a ($C_1$-$C_6$)carbonyloxy ($C_1$-$C_6$)alkyl group or a di($C_1$-$C_6$)alkylaminocarbonyl ($C_1$-$C_6$)alkyl group, A represents the group

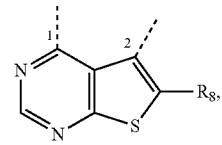

wherein 1 is linked to the oxygen atom and 2 is linked to the phenyl ring, $R_1$ represents a linear or branched ($C_1$-$C_6$)alkyl group, a linear or branched ($C_2$-$C_6$)alkenyl group, a linear or branched ($C_2$-$C_6$)alkynyl group, a linear or branched ($C_1$-$C_6$)alkoxy group, a —S—($C_1$-$C_6$)alkyl group, a linear or branched ($C_1$-$C_6$)polyhaloalkyl, a hydroxy group, a hydroxy($C_1$-$C_6$)alkyl group, a cyano group, —$NR_{11}R_{11}'$, —$Cy_6$, or a halogen atom, $R_3$ represents a hydrogen atom, a halogen atom, a linear or branched ($C_1$-$C_6$)alkyl group, a linear or branched ($C_2$-$C_6$)alkenyl group, a linear or branched ($C_2$-$C_6$) alkynyl group, a linear or branched ($C_1$-$C_6$)polyhaloalkyl, a hydroxy group, a hydroxy($C_1$-$C_6$)alkyl group, a linear or branched ($C_1$-$C_6$)alkoxy group, a —S—($C_1$-$C_6$)alkyl group, a cyano group, a nitro group, -alkyl($C_0$-$C_6$)—$NR_9R_9'$, —O-alkyl($C_1$-$C_6$)—$NR_9R_9'$, —O-alkyl($C_1$-$C_6$)—$R_{10}$, —C(O)—$OR_9$, —O—C(O)—$R_9$, —C(O)—$NR_9R_9'$, —$NR_9$—C(O)—$R_9'$, —$NR_9$—C(O)—$OR_9'$, -alkyl($C_1$-$C_6$)—$NR_9$—C(O)—$R_{10}'$, —$SO_2$—$NR_9R_9'$, —$SO_2$—alkyl($C_1$-$C_6$), $R_6$ and $R_7$ independently of one another represent a hydrogen atom, a halogen atom, a linear or branched ($C_1$-$C_6$)alkyl group, a linear or branched ($C_2$-$C_6$)alkenyl group, a linear or branched ($C_2$-$C_6$)alkynyl group, a linear or branched ($C_1$-$C_6$)polyhaloalkyl, a hydroxy group, a linear or branched ($C_1$-$C_6$)alkoxy group, a —S—($C_1$-$C_6$)alkyl group, a cyano group, a nitro group, -alkyl($C_0$-$C_6$)—$NR_9R_9'$, —O-alkyl($C_1$-$C_6$)—$NR_9R_9'$, —O—$Cy_1$, -alkyl($C_0$-$C_6$)—$Cy_1$, -alkenyl($C_2$-$C_6$)—$Cy_1$, -alkynyl($C_2$-$C_6$)—$Cy_1$, —O-alkyl($C_1$-$C_6$)—$R_{10}$, —C(O)—$OR_9$, —O—C(O)—$R_9$, —C(O)—$NR_9R_9'$, —$NR_9$—C(O)—$R_9'$, —$NR_9$—C(O)—$OR_9'$, -alkyl($C_1$-$C_6$)—$NR_9$—C(O)—$R_9'$, —$SO_2$—$NR_9R_9'$, —$SO_2$-alkyl($C_1$-$C_6$), or the substituents of the pair ($R_6$, $R_7$), when grafted onto two adjacent carbon atoms, together with the carbon atoms carrying them, form an aromatic or non-aromatic ring having from 5 to 7 ring members, which ring may contain from 1 to 3 heteroatoms selected from oxygen, sulphur and nitrogen, wherein the resulting ring may be substituted by a group selected from the group consisting of a linear or branched ($C_1$-$C_6$)alkyl group, —$NR_{11}R_{11}'$, -alkyl($C_0$-$C_6$)—$Cy_1$, and oxo, $R_8$ represents a linear or branched ($C_1$-$C_6$)alkyl group, a linear or branched ($C_2$-$C_6$)alkenyl group, a linear or branched ($C_2$-$C_6$)alkynyl group, —$Cy_3$, -alkyl($C_1$-$C_6$)—$Cy_3$, -alkenyl($C_2$-$C_6$)—$Cy_3$, -alkynyl($C_2$-$C_6$)—$Cy_3$, —$Cy_3$-$Cy_4$, -alkynyl($C_2$-$C_6$)—O—$Cy_3$, —$Cy_3$-alkyl($C_0$-$C_6$)—O-alkyl($C_0$-$C_6$)—$Cy_4$, a halogen atom, a cyano group, —C(O)—$R_{12}$, or —C(O)—$NR_{12}R_{12}'$, $R_9$ and $R_9'$ independently of one another represent a hydrogen atom, a linear or branched ($C_1$-$C_6$)alkyl group, -alkyl($C_0$-$C_6$)—$Cy_1$, or the substituents of the pair ($R_9$, $R_9'$), together with the nitrogen atom carrying them, form an aromatic or non-aromatic ring having from 5 to 7 ring members, which ring may contain, in addition to the nitrogen atom, from 1 to 3 heteroatoms selected from oxygen, sulphur and nitrogen, wherein the nitrogen may be substituted by a hydrogen atom or a linear or branched ($C_1$-$C_6$)alkyl group and wherein one or more of the carbon atoms of the possible substituents, may be deuterated, $R_{10}$ represents —$Cy_1$, —$Cy_1$-alkyl($C_0$-$C_6$)-$Cy_2$, —$Cy_1$-alkyl($C_0$-$C_6$)—O-alkyl($C_0$-$C_6$)—$Cy_2$, —$Cy_1$-alkyl($C_0$-$C_6$)—$NR_9$-alkyl($C_0$-$C_6$)—$Cy_2$, —$Cy_1$-$Cy_2$-O-alkyl($C_0$-$C_6$)—$Cy_5$, —C(O)—$NR_9R_9'$, —$NR_9R_9'$, —$OR_9$, —$NR_9$—C(O)—$R_9'$, —O-alkyl($C_1$-$C_6$)—$OR_9$, —$SO_2$—$R_9$, —C(O)—$OR_9$, or —NH—C(O)—NH—$R_7$, $R_{11}$, $R_{11}'$, $R_{12}$ and $R_{12}'$, independently of one another represent a hydrogen atom or an optionally substituted linear or branched ($C_1$-$C_6$)alkyl group, $R_{13}$ represents a hydrogen atom, a hydroxy group, or a hydroxy($C_1$-$C_6$)alkyl group, $Cy_1$, $Cy_2$, $Cy_3$, $Cy_4$, $Cy_5$ and $Cy_6$, independently of one another, represent a cycloalkyl group, a heterocycloalkyl group, an aryl group or a heteroaryl group, and n is an integer equal to 0 or 1, wherein:

"aryl" means a phenyl, naphthyl, biphenyl, indanyl or indenyl group,

"heteroaryl" means any mono- or bi-cyclic group composed of from 5 to 10 ring members, having at least one aromatic moiety and containing from 1 to 3 heteroatoms selected from oxygen, sulphur and nitrogen, "cycloalkyl" means any mono- or bi-cyclic non-aromatic carbocyclic group containing from 3 to 10 ring members, "heterocycloalkyl" means any mono- or bi-cyclic non-aromatic carbocyclic group containing from 3 to 10 ring members, and containing from 1 to 3 heteroatoms selected from oxygen, sulphur and nitrogen, which may include fused, bridged or spiro ring systems, wherein the aryl, heteroaryl, cycloalkyl and heterocycloalkyl groups so defined and the alkyl, alkenyl, alkynyl, alkoxy groups, may be substituted by from 1 to 4 groups selected from linear or branched ($C_1$-$C_6$)alkyl, linear or branched ($C_2$-$C_6$)alkenyl group, linear or branched ($C_2$-$C_6$)alkynyl group, linear or branched ($C_1$-$C_6$)alkoxy, ($C_1$-$C_6$) alkyl-S—, hydroxy, oxo (or N-oxide where appropriate), nitro, cyano, —C(O)—OR', —O—C(O)—R', —C(O)—NR'R", —NR'R", —(C=NR')—OR", linear or branched ($C_1$-$C_6$)polyhaloalkyl, trifluoromethoxy, or halogen, wherein R' and R", independently of one another, represent a hydrogen atom or a linear or branched ($C_1$-$C_6$)alkyl group, and wherein one or more of the carbon atoms of the preceding possible substituents, may be deuterated, and wherein the substituents of the pair ($R_1$, $R_5'$) are identical, its enantiomers, diastereoisomers and atropisomers, or a pharmaceutically acceptable salt thereof.

28. A compound of formula ($VII_B$):

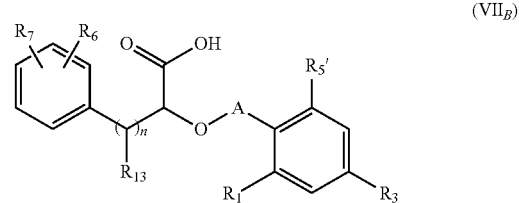

wherein:

$R_5'$ represents a halogen atom, a linear or branched ($C_1$-$C_6$)alkyl group, a linear or branched ($C_2$-$C_6$)alkenyl group, a linear or branched ($C_2$-$C_6$)alkynyl group, a linear or branched ($C_1$-$C_6$)polyhaloalkyl, a hydroxy group, a hydroxy($C_1$-$C_6$)alkyl group, a linear or branched ($C_1$-$C_6$)alkoxy group, a —S—($C_1$-$C_6$)alkyl group, a cyano group, a nitro group, -alkyl($C_0$-$C_6$)—$NR_9R_9'$, —O-alkyl($C_1$-$C_6$)—$NR_9R_9'$, —O-alkyl($C_1$-$C_6$)—$R_{10}$, —C(O)—$OR_9$, —O—C(O)—$R_9$, —C(O)—$NR_9R_9'$, —$NR_9$—C(O)—$R_9'$, —$NR_9$—C(O)—$OR_9'$, -alkyl($C_1$-$C_6$)—$NR_9$—C(O)—$R_9'$, —$SO_2$—$NR_9R_9'$, —$SO_2$-alkyl($C_1$-$C_6$), A represents the group

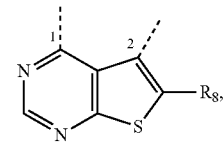

wherein 1 is linked to the oxygen atom and 2 is linked to the phenyl ring, $R_1$ represents a linear or branched $(C_1-C_6)$alkyl group, a linear or branched $(C_2-C_6)$alkenyl group, a linear or branched $(C_2-C_6)$alkynyl group, a linear or branched $(C_1-C_6)$alkoxy group, a —S—$(C_1-C_6)$alkyl group, a linear or branched $(C_1-C_6)$polyhaloalkyl, a hydroxy group, a hydroxy$(C_1-C_6)$alkyl group, a cyano group, —$NR_{11}R_{11}'$, —$Cy_6$, or a halogen atom, $R_3$ represents a hydrogen atom, a halogen atom, a linear or branched $(C_1-C_6)$alkyl group, a linear or branched $(C_2-C_6)$alkenyl group, a linear or branched $(C_2-C_6)$alkynyl group, a linear or branched $(C_1-C_6)$polyhaloalkyl, a hydroxy group, a hydroxy$(C_1-C_6)$alkyl group, a linear or branched $(C_1-C_6)$alkoxy group, a —S—$(C_1-C_6)$alkyl group, a cyano group, a nitro group, -alkyl$(C_0-C_6)$—$NR_9R_9'$, —O-alkyl$(C_1-C_6)$—$NR_9R_9'$, —O-alkyl$(C_1-C_6)$—$R_{10}$, —C(O)—$OR_9$, —O—C(O)—$R_9$, —C(O)—$NR_9R_9'$, —$NR_9$—C(O)—$R_9'$, —$NR_9$—C(O)—$OR_9'$, -alkyl$(C_1-C_6)$—$NR_9$—C(O)—$R_9'$, —$SO_2$—$NR_9R_9'$, —$SO_2$-alkyl$(C_1-C_6)$, $R_6$ and $R_7$ independently of one another represent a hydrogen atom, a halogen atom, a linear or branched $(C_1-C_6)$alkyl group, a linear or branched $(C_2-C_6)$alkenyl group, a linear or branched $(C_2-C_6)$alkynyl group, a linear or branched $(C_1-C_6)$polyhaloalkyl, a hydroxy group, a linear or branched $(C_1-C_6)$alkoxy group, a —S—$(C_1-C_6)$alkyl group, a cyano group, a nitro group, -alkyl$(C_0-C_6)$—$NR_9R_9'$, —O-alkyl$(C_1-C_6)$—$NR_9R_9'$, —O—$Cy_1$, -alkyl$(C_0-C_6)$—$Cy_1$, -alkenyl$(C_2-C_6)$-$Cy_1$, -alkynyl$(C_2-C_6)$—$Cy_1$, —O-alkyl$(C_1-C_6)$—$R_{10}$, —C(O)—$OR_9$, —O—C(O)—$R_9$, —C(O)—$NR_9R_9'$, —$NR_9$—C(O)—$R_9'$, —$NR_9$—C(O)—$OR_9'$, -alkyl$(C_1-C_6)$—$NR_9$—C(O)—$R_9'$, —$SO_2$—$NR_9R_9'$, —$SO_2$-alkyl$(C_1-C_6)$, or the substituents of the pair $(R_6, R_7)$, when grafted onto two adjacent carbon atoms, together with the carbon atoms carrying them, form an aromatic or non-aromatic ring having from 5 to 7 ring members, which ring may contain from 1 to 3 heteroatoms selected from oxygen, sulphur and nitrogen, wherein the resulting ring may be substituted by a group selected from the group consisting of a linear or branched $(C_1-C_6)$alkyl group, —$NR_{11}R_{11}'$, -alkyl$(C_0-C_6)$—$Cy_1$, and oxo, $R_8$ represents a linear or branched $(C_1-C_6)$alkyl group, a linear or branched $(C_2-C_6)$alkenyl group, a linear or branched $(C_2-C_6)$alkynyl group, —$Cy_3$, -alkyl$(C_1-C_6)$-$Cy_3$, -alkenyl$(C_2-C_6)$-$Cy_3$, -alkynyl$(C_2-C_6)$-$Cy_3$, —$Cy_3$-$Cy_4$, -alkynyl$(C_2-C_6)$—O-$Cy_3$, —$Cy_3$-alkyl$(C_0-C_6)$—O-alkyl$(C_0-C_6)$—$Cy_4$, a halogen atom, a cyano group, —C(O)—$R_{12}$, or —C(O)—$NR_{12}R_{12}'$, $R_9$ and $R_9'$ independently of one another represent a hydrogen atom, a linear or branched $(C_1-C_6)$alkyl group, -alkyl$(C_0-C_6)$—$Cy_1$, or the substituents of the pair $(R_9, R_9')$, together with the nitrogen atom carrying them, form an aromatic or non-aromatic ring having from 5 to 7 ring members, which ring may contain, in addition to the nitrogen atom, from 1 to 3 heteroatoms selected from oxygen, sulphur and nitrogen, wherein the nitrogen may be substituted by a hydrogen atom or a linear or branched $(C_1-C_6)$alkyl group and wherein one or more of the carbon atoms of the possible substituents, may be deuterated, $R_{10}$ represents —$Cy_1$, —$Cy_1$-alkyl$(C_0-C_6)$—$Cy_2$, —$Cy_1$-alkyl$(C_0-C_6)$—O-alkyl$(C_0-C_6)$—$Cy_2$, —$Cy_1$-alkyl$(C_0-C_6)$—$NR_9$-alkyl$(C_0-C_6)$—$Cy_2$, —$Cy_1$-$Cy_2$-O-alkyl$(C_0-C_6)$—$Cy_5$, —C(O)—$NR_9R_9'$, —$NR_9R_9'$, —$OR_9$, —$NR_9$—C(O)—$R_9'$, —O-alkyl$(C_1-C_6)$—$OR_9$, —$SO_2$—$R_9$, —C(O)—$OR_9$, or —NH—C(O)—NH—$R_7$, $R_{11}$, $R_{11}'$, $R_{12}$ and $R_{12}'$, independently of one another represent a hydrogen atom or an optionally substituted linear or branched $(C_1-C_6)$alkyl group, $R_{13}$ represents a hydrogen atom, a hydroxy group, or a hydroxy$(C_1-C_6)$alkyl group, $Cy_1$, $Cy_2$, $Cy_3$, $Cy_4$, $Cy_5$ and $Cy_6$, independently of one another, represent a cycloalkyl group, a heterocycloalkyl group, an aryl group or a heteroaryl group, and n is an integer equal to 0 or 1, wherein:
"aryl" means a phenyl, naphthyl, biphenyl, indanyl or indenyl group,
"heteroaryl" means any mono- or bi-cyclic group composed of from 5 to 10 ring members, having at least one aromatic moiety and containing from 1 to 3 heteroatoms selected from oxygen, sulphur and nitrogen,
"cycloalkyl" means any mono- or bi-cyclic non-aromatic carbocyclic group containing from 3 to 10 ring members,
"heterocycloalkyl" means any mono- or bi-cyclic non-aromatic carbocyclic group containing from 3 to 10 ring members, and containing from 1 to 3 heteroatoms selected from oxygen, sulphur and nitrogen, which may include fused, bridged or spiro ring systems, wherein the aryl, heteroaryl, cycloalkyl and heterocycloalkyl groups so defined and the alkyl, alkenyl, alkynyl, alkoxy groups, may be substituted by from 1 to 4 groups selected from linear or branched $(C_1-C_6)$alkyl, linear or branched $(C_2-C_6)$alkenyl group, linear or branched $(C_2-C_6)$alkynyl group, linear or branched $(C_1-C_6)$alkoxy, $(C_1-C_6)$alkyl-S—, hydroxy, oxo (or N-oxide where appropriate), nitro, cyano, —C(O)—OR', —O—C(O)—R', —C(O)—NR'R", —NR'R", —(C=NR')—OR", linear or branched $(C_1-C_6)$polyhaloalkyl, trifluoromethoxy, or halogen, wherein R' and R", independently of one another, represent a hydrogen atom or a linear or branched $(C_1-C_6)$alkyl group, and wherein one or more of the carbon atoms of the preceding possible substituents, may be deuterated, and wherein the substituents of the pair $(R_1, R_5')$ are identical, its enantiomers, diastereoisomers and atropisomers, or a pharmaceutically acceptable salt thereof.

29. The compound according to claim 28, which is (2R)-2-{[5-{2,6-dimethyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid.

30. A pharmaceutical composition comprising the compound according to claim 1, or an addition salt thereof with a pharmaceutically acceptable acid or base in combination with one or more pharmaceutically acceptable excipients.

31. A combination of the compound according to claim 1, with an anti-cancer agent selected from genotoxic agents, mitotic poisons, anti-metabolites, proteasome inhibitors, kinase inhibitors and antibodies.

32. A pharmaceutical composition comprising the combination according to claim 31, in combination with one or more pharmaceutically acceptable excipients.

33. A pharmaceutical composition comprising the compound according to claim 22, or an addition salt thereof with a pharmaceutically acceptable acid or base in combination with one or more pharmaceutically acceptable excipients.

34. A combination of the compound according to claim 22, with an anti-cancer agent selected from genotoxic agents, mitotic poisons, anti-metabolites, proteasome inhibitors, kinase inhibitors and antibodies.

35. A pharmaceutical composition comprising the combination according to claim 34, in combination with one or more pharmaceutically acceptable excipients.

36. A pharmaceutical composition comprising t compound according to claim 24, or an addition salt thereof with a pharmaceutically acceptable acid or base in combination with one or more pharmaceutically acceptable excipients.

37. A combination of the compound according to claim 24, with an anti-cancer agent selected from genotoxic agents, mitotic poisons, anti-metabolites, proteasome inhibitors, kinase inhibitors and antibodies.

38. A pharmaceutical composition comprising the combination according to claim 37, in combination with one or more pharmaceutically acceptable excipients.

39. A pharmaceutical composition comprising the compound according to claim 27, or an addition salt thereof with a pharmaceutically acceptable acid or base in combination with one or more pharmaceutically acceptable excipients.

40. A combination of the compound according to claim 27, with an anti-cancer agent selected from genotoxic agents, mitotic poisons, anti-metabolites, proteasome inhibitors, kinase inhibitors and antibodies.

41. A pharmaceutical composition comprising the combination according to claim 40, in combination with one or more pharmaceutically acceptable excipients.

42. A pharmaceutical composition comprising the compound according to claim 28, or an addition salt thereof with a pharmaceutically acceptable acid or base in combination with one or more pharmaceutically acceptable excipients.

43. A combination of the compound according to claim 28, with an anti-cancer agent selected from genotoxic agents, mitotic poisons, anti-metabolites, proteasome inhibitors, kinase inhibitors and antibodies.

44. A pharmaceutical composition comprising the combination according to claim 43, in combination with one or more pharmaceutically acceptable excipients.

* * * * *

UNITED STATES PATENT AND TRADEMARK OFFICE
CERTIFICATE OF CORRECTION

PATENT NO. : 10,227,358 B2
APPLICATION NO. : 15/737479
DATED : March 12, 2019
INVENTOR(S) : Zoltán Szlávik et al.

Page 1 of 1

It is certified that error appears in the above-identified patent and that said Letters Patent is hereby corrected as shown below:

On the Title Page

Under Assignees, Line 2: "&R&D)" should read -- (R&D) --.

In the Claims

Column 36, Line 19 Claim 1: insert -- A -- before "represents".

Column 40, Line 43 Claim 21: "$\{[5S_o)$" should read -- $\{[5S_a)$ --.
    Line 53 Claim 21: "1-$\{[((octyloxy)$" should read -- 1-$\{[(octyloxy)$ --.

Column 43, Line 63 Claim 22: insert -- and atropisomers -- before "or".

Column 51, Line 8 Claim 36: "t com-" should read -- the com- --.

Signed and Sealed this
Twenty-first Day of May, 2019

Andrei Iancu
*Director of the United States Patent and Trademark Office*